(12) United States Patent
Kishima et al.

(10) Patent No.: US 11,532,250 B2
(45) Date of Patent: Dec. 20, 2022

(54) INFORMATION PROCESSING DEVICE, INFORMATION PROCESSING METHOD, SCREEN, AND INFORMATION DRAWING SYSTEM

(71) Applicant: SONY CORPORATION, Tokyo (JP)

(72) Inventors: Koichiro Kishima, Kanagawa (JP); Akio Furukawa, Tokyo (JP); Hiroshi Maeda, Kanagawa (JP); Naoto Nakamura, Kanagawa (JP); Georgero Konno, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 203 days.

(21) Appl. No.: 16/475,204

(22) PCT Filed: Oct. 30, 2017

(86) PCT No.: PCT/JP2017/039158
§ 371 (c)(1),
(2) Date: Jul. 1, 2019

(87) PCT Pub. No.: WO2018/131262
PCT Pub. Date: Jul. 19, 2018

(65) Prior Publication Data
US 2019/0340963 A1 Nov. 7, 2019

(30) Foreign Application Priority Data

Jan. 11, 2017 (JP) .............................. JP2017-002707

(51) Int. Cl.
*G09G 3/00* (2006.01)
*A61B 34/00* (2016.01)
(Continued)

(52) U.S. Cl.
CPC ............ *G09G 3/001* (2013.01); *A61B 5/7445* (2013.01); *A61B 34/25* (2016.02); *G03B 21/60* (2013.01);
(Continued)

(58) Field of Classification Search
CPC ....... G09G 3/001; A61B 34/25; A61B 5/7445; A61B 2034/254; A61B 2034/256;
(Continued)

(56) References Cited

U.S. PATENT DOCUMENTS

| 4,944,311 A | * | 7/1990 | Eldridge, Jr. | .......... A61B 46/23 128/849 |
| 2003/0046562 A1 | * | 3/2003 | Uchikubo | .............. A61B 1/042 713/189 |

(Continued)

FOREIGN PATENT DOCUMENTS

| EP | 3142358 A1 | 3/2017 |
| JP | 2005-292453 A | 10/2005 |

(Continued)

OTHER PUBLICATIONS

International Search Report and Written Opinion of PCT Application No. PCT/JP2017/039158, dated Jan. 16, 2018, 15 pages of ISRWO.

(Continued)

*Primary Examiner* — Ifedayo B Iluyomade
(74) *Attorney, Agent, or Firm* — Chip Law Group

(57) ABSTRACT

There is provided an information processing device including an information acquisition unit that acquires information from an information providing device that provides the information related to quantitative numerical values to be grasped by the medical practitioner involved with a medical practice, an image data generation unit that generates image data related to the acquired information, and a control unit (Continued)

| MEDICAL PRACTICE | INFORMATION TO BE SELECTED |
|---|---|
| INCISION | AMOUNT OF BLEEDING, SETTING VALUE OF ELECTRIC KNIFE |
| ARTERIAL BLOCKADE | ELAPSED TIME FROM ARTERIAL BLOCKADE |
| OPENING STOMACH | NUMBER OF GAUZE SHEETS |
| ⋮ | ⋮ | that controls an installation position of a light source irradiating drawing light having illuminance visually recognizable under a shadowless lamp or an operation state of an optical system that scans an irradiation position of the drawing light so as to draw the image data.

16 Claims, 19 Drawing Sheets

(51) Int. Cl.
  *G03B 21/60* (2014.01)
  *A61B 5/02* (2006.01)
  *A61B 5/021* (2006.01)
  *A61B 5/024* (2006.01)
  *A61B 18/14* (2006.01)
  *A61B 5/00* (2006.01)

(52) U.S. Cl.
  CPC ............... *A61B 5/021* (2013.01); *A61B 5/024* (2013.01); *A61B 5/02042* (2013.01); *A61B 18/14* (2013.01); *A61B 2034/254* (2016.02); *A61B 2034/256* (2016.02)

(58) Field of Classification Search
  CPC ........... A61B 5/00; A61B 5/021; A61B 5/024; A61B 5/02042; A61B 18/14; A61B 90/00; G03B 21/60; G16H 40/60; H04N 5/74
  USPC ......................................................... 345/204
  See application file for complete search history.

(56) References Cited

U.S. PATENT DOCUMENTS

| | | | |
|---|---|---|---|
| 2006/0050188 A1* | 3/2006 | Miyaki ..................... | B24C 1/06 349/5 |
| 2010/0265193 A1* | 10/2010 | Kung ..................... | G06F 3/0445 345/173 |
| 2014/0031659 A1* | 1/2014 | Zhao ........................ | A61B 1/07 600/371 |
| 2014/0275851 A1* | 9/2014 | Amble ................. | A61B 5/7425 600/301 |
| 2015/0081295 A1* | 3/2015 | Yun ......................... | G06F 21/32 704/236 |
| 2015/0305828 A1* | 10/2015 | Park ....................... | A61B 34/25 345/629 |
| 2016/0188813 A1* | 6/2016 | Hennenfent ........... | G16H 40/20 705/2 |
| 2017/0094236 A1* | 3/2017 | Kiriyama ............... | H04N 5/332 |
| 2017/0249552 A1* | 8/2017 | Boss ....................... | G06N 20/00 |

FOREIGN PATENT DOCUMENTS

| | | |
|---|---|---|
| JP | 2015012992 A | 1/2015 |
| JP | 2016-027687 A | 2/2016 |
| WO | 2015/198529 A1 | 12/2015 |

OTHER PUBLICATIONS

Office Action issued in Japanese Patent Appln. No. 2018-561821 dated Apr. 27, 2021.

* cited by examiner

| MEDICAL PRACTICE | INFORMATION TO BE SELECTED |
|---|---|
| INCISION | AMOUNT OF BLEEDING, SETTING VALUE OF ELECTRIC KNIFE |
| ARTERIAL BLOCKADE | ELAPSED TIME FROM ARTERIAL BLOCKADE |
| OPENING STOMACH | NUMBER OF GAUZE SHEETS |
| ⋮ | ⋮ |

INFORMATION PROCESSING DEVICE, INFORMATION PROCESSING METHOD, SCREEN, AND INFORMATION DRAWING SYSTEM

CROSS REFERENCE TO RELATED APPLICATIONS

This application is a U.S. National Phase of International Patent Application No. PCT/JP2017/039158 filed on Oct. 30, 2017, which claims priority benefit of Japanese Patent Application No. JP 2017-002707 filed in the Japan Patent Office on Jan. 11, 2017. Each of the above-referenced applications is hereby incorporated herein by reference in its entirety.

TECHNICAL FIELD

The present disclosure relates to an information processing device, an information processing method, a program, a screen, and an information drawing system.

BACKGROUND ART

In various types of surgery and the like, the operator checks various information such as biological information of a patient such as blood pressure, heart rate, and an amount of bleeding, or a setting value of a medical instrument from an assistant such as an anesthesiologist or a nurse and performs the surgical operation while storing the information provided by the assistant. Such providing of the information from the assistant to the operator is mainly transmitted by oral communication. This is because the surgical site on which the surgical operation is performed needs to be clean, and thus the assistant near the operator cannot present information to the operator in such a way as writing a memo or the like to impair the cleanliness of the surgical site. In addition, since the surgical operation is generally performed under a shadowless lamp, even if the assistant writes a memo and presents the memo to the operator, the flat glossy surface strongly reflects the shadowless lamp, and thus, in some cases, it maybe difficult for the operator to check the memo.

Regarding such information transmission, Patent Document 1 discloses a display device for providing information to an operator. The display device disclosed in Patent Document 1 includes a light shielding plate that shields light of a shadowless lamp, and a panel for displaying the information is installed at a position shielded by the light shielding plate.

CITATION LIST

Patent Document

Patent Document 1: Japanese Patent Application Laid-Open No. 2005-292453

SUMMARY OF THE INVENTION

Problems to be Solved by the Invention

In a display device disclosed in Patent Document 1, although an operator can visually recognize information, since illumination light from a shadowless lamp is shielded, there is a possibility that illuminance at the surgical site is insufficient. Therefore, in the present disclosure, an information processing device, an information processing method, a program, a screen, and an information drawing system are proposed which can provide information to an operator more reliably even under a shadowless lamp.

Solutions to Problems

According to the present disclosure, there is provided an information processing device including: an information acquisition unit that acquires information from an information providing device that provides the information related to quantitative numerical values to be grasped by a medical practitioner involved with a medical practice; an image data generation unit that generates image data related to the acquired information; and a control unit that controls an installation position of a light source irradiating drawing light having illuminance visually recognizable under a shadowless lamp or an operation state of an optical system that scans an irradiation position of the drawing light so as to draw the image data.

In addition, according to the present disclosure, there is provided an information processing method including: acquiring information from an information providing device that provides the information related to a medical practice or a condition of a patient; generating image data related to the acquired information; and controlling an installation position of a light source irradiating drawing light having illuminance visually recognizable under a shadowless lamp or an operation state of an optical system that scans an irradiation position of the drawing light so as to draw the image data.

In addition, according to the present disclosure, there is provided a program causing a processor to execute: acquiring information from an information providing device that provides the information related to a medical practice or a condition of a patient; generating image data related to the acquired information; and controlling an installation position of a light source irradiating drawing light having illuminance visually recognizable under a shadowless lamp or an operation state of an optical system that scans an irradiation position of the drawing light so as to draw the image data.

In addition, according to the present disclosure, there is provided a screen including: a substrate including a predetermined material; and a selective reflection layer having a reflectance for a wavelength of drawing light from an information drawing device that draws an image by using the drawing light having illuminance visually recognizable under a shadowless lamp, the reflectance being higher than a reflectance for wavelengths of other light, on the substrate.

In addition, according to the present disclosure, there is provided an information drawing system including: an information drawing device including: a light source that irradiates drawing light having illuminance visually recognizable under a shadowless lamp; an optical system that scans an irradiation position of the drawing light; an information acquisition unit that acquires information from an information providing device that provides the information related to quantitative numerical values to be grasped by a medical practitioner involved with a medical practice; an image data generation unit that generates image data related to the acquired information; and a control unit that controls an installation position of the light source or an operation state of the optical system so as to draw the image data; and a screen including: a substrate including a predetermined material; and a selective reflection layer having a reflectance for a wavelength of the drawing light from the information drawing device, the reflectance being higher than a reflectance for a wavelength of other light, on the substrate.

Effects of the Invention

As described above, according to the present disclosure, it is possible to more reliably provide information to an operator even under a shadowless lamp.

In addition, the above-described effects are not necessarily limited, and any of the effects illustrated in the present specification or other effects that can be grasped from the present specification may be exhibited together with the above effects or in place of the above effects.

MODE FOR CARRYING OUT THE INVENTION

Figure 1:
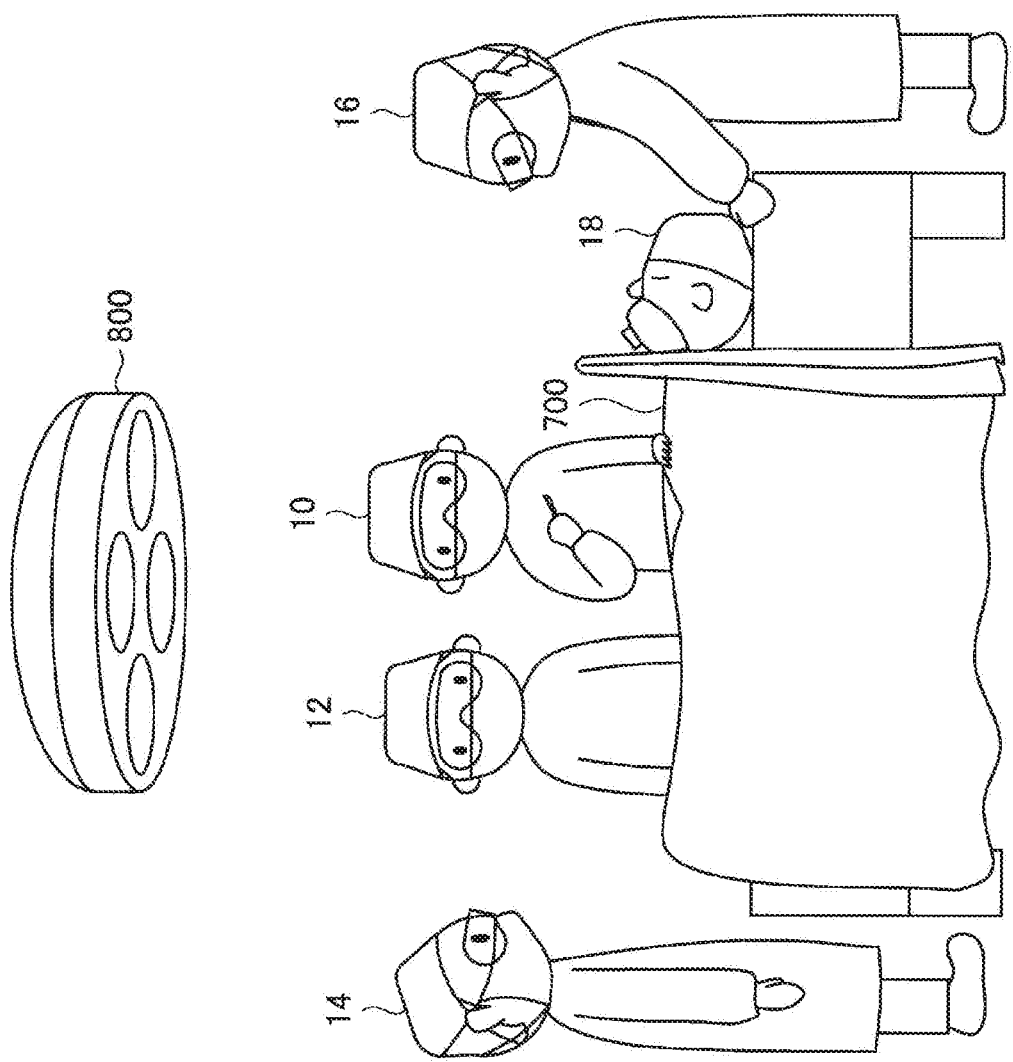
FIG. 1 is a diagram illustrating a general surgical environment.

Hereinafter, preferred embodiments of the present disclosure will be described in detail with reference to the accompanying drawings. In addition, in the present specification and the drawings, components having substantially the same functional configuration will be denoted by the same reference numerals, and redundant description thereof will be omitted.

In addition, the description will be made in the following order.

0. General Surgery Environment
1. Configuration Example of Information Drawing System
  1-1. Whole Configuration of Information Drawing System
  1-2. Configuration Example of Controller
  1-3. Processing Example of Controller
2. Screen
  2-1. Configuration of Screen
  2-2. Installation Method of Screen
  2-3. Other Configuration Examples of Screen
3. Hardware Configuration
4. Supplement
5. Conclusion 0. General Surgery Environment FIG. 1 is a schematic diagram illustrating an environment of a general surgery room. In a typical surgical environment, a patient 18 covered with drape 700 lies on an operating table under a shadowless lamp 800, and a plurality of medical practitioners are positioned to surround the patient 18. As a medical practitioner, for example, there is an operator 10 who performs a surgical operation, there is an instrument transfer assistant 12 who transfers an instrument used in the surgical operation to the operator 10, there is an outer circumference assistant 14 who sets a setting value of the medical instrument in response to instruction of the operator 10, and there is an anesthesiologist 16 who performs controlling anesthesia. In addition, the above-described medical practitioners are examples, and the present disclosure is not limited to these medical practitioners.

In the environment as described above, in some cases, for example, the operator 10 instructs the anesthesiologist 16 to raise the blood pressure and checks with the anesthesiologist 16 whether or not the value of the blood pressure has become the value instructed by the operator 10. In addition, in some cases, the operator 10 instructs the outer circumference assistant 14 to change the settings of the medical instrument and checks with the outer circumference assistant 14 whether or not the setting value of the medical instrument has become the value instructed by the operator 10.

It is considered that the presentation of the information in response to the instruction from the operator 10 as described above is made by a memo. However, since the instrument transfer assistant 12 who transfers the medical instrument to the operator 10 touches the device used for the surgical operation, the instrument transfer assistant cannot touch other dirty objects and cannot take a memo. In addition, the outer circumference assistant 14 may touch something that is not clean, but the outer circumference assistant cannot touch something that is clean. Therefore, even if the memo is taken, the outer circumference assistant 14 cannot present the memo near a surgical field that needs to be clean. In addition, even if the instrument transfer assistant 12 or the outer circumference assistant 14 presents a memo on white paper to the operator 10, the reflectance of light is strong under the shadowless lamp 800, so that it is difficult for the operator 10 to visually recognize the memo. In addition, since it is preferable that the operator 10 is able to gaze at the surgical field, it is not preferable to move the line of sight to a large degree in order to visually recognize the memo.

Therefore, the instruction and the checking as described above are mainly performed by oral communication at any time, and the operator 10 acquires information by oral communication and performs the surgical operation while storing the quantitative numerical values.

In addition, in some cases, a medical instrument such as an electric knife that may generate noise may be installed at a position away from the outer circumference assistant 14, and thus, it may take much time for the outer circumference assistant 14 to check the setting values. Since the operator 10 has to stop the progress of the surgery in such a situation until the outer circumference assistant 14 checks the setting values, a time loss occurs in the progress of the surgery.

Therefore, in the present embodiment, an information drawing system capable of providing quantitative numerical values to be grasped by the operator 10 without causing the operator 10 to greatly move the line of sight from a surgical field is proposed.

1. Configuration Example of Information Drawing System

<1-1. Overall Configuration of Information Drawing System>

Figure 2:
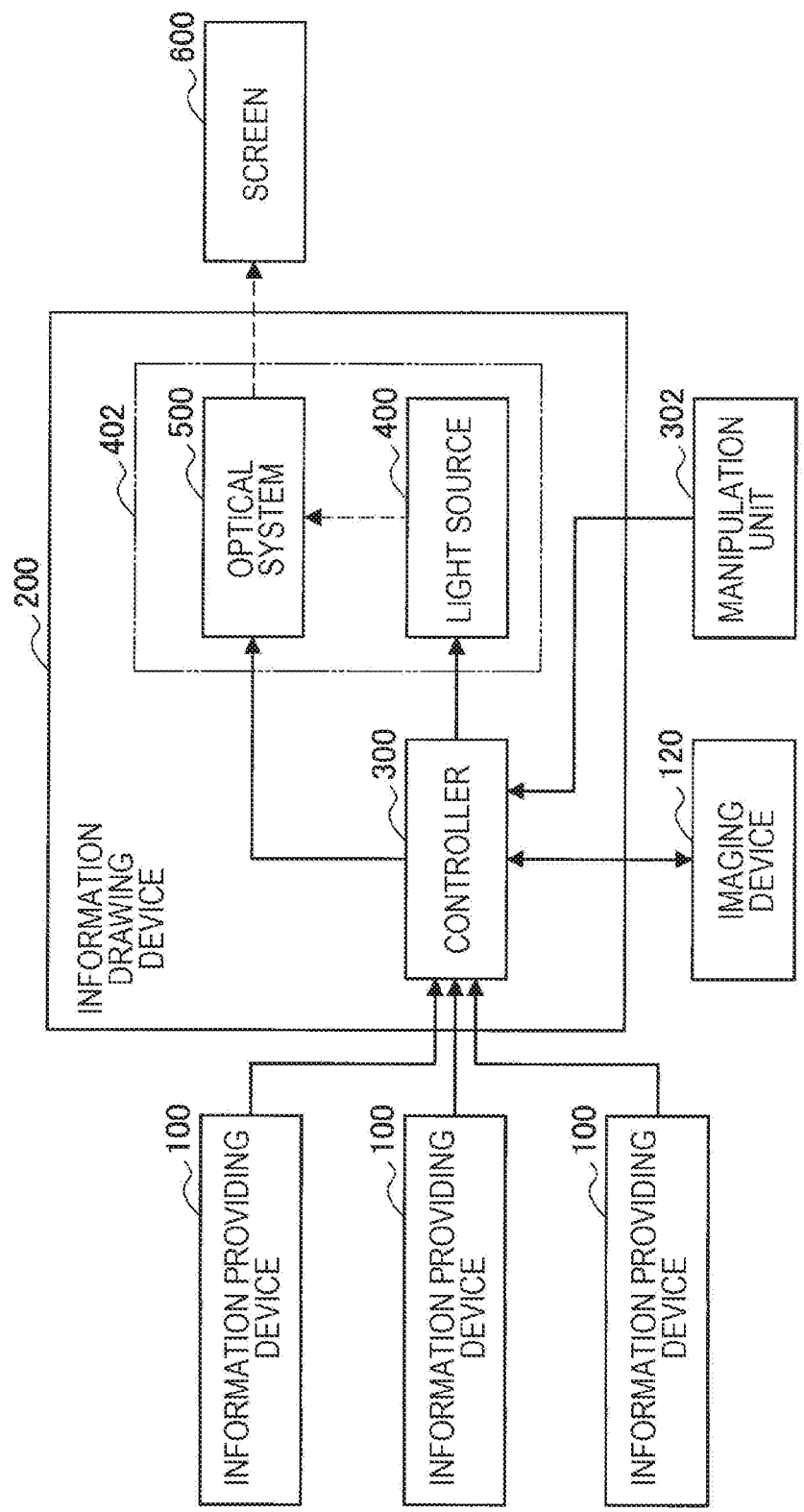
FIG. 2 is a block diagram illustrating an example of a configuration of an information drawing system according to an embodiment of the present disclosure.

FIG. 2 is a diagram illustrating an example of an overall configuration of the information drawing system according to the present embodiment. The information drawing system according to the present embodiment is a system that draws, on a screen 600, quantitative numerical values to be grasped by the operator 10 such as biological information of the patient 18 such as blood pressure, setting values of a medical instrument such as an electric knife or an ultrasonic knife, or an angle of an operating table.

As illustrated in FIG. 2, the information drawing system includes a screen 600 and an information drawing device 200 that receives information from a plurality of information providing devices 100 and irradiates the screen 600 with drawing light. In addition, the information drawing system may include an imaging device 120 for imaging information displayed on the information providing device 100 and a manipulation unit 302 manipulated by the medical practitioner. The information providing device 100 is, for example, a device that provides quantitative numerical values to be grasped by the operator 10, such as a device that measures blood pressure, a device that measures an amount of bleeding, a device that sets a mode and an output value of an electric knife, and a time measurement device. The information providing device 100 may provide header information indicating what kind of information the provided numerical information is together with the numerical information to the information drawing device 200. The header information is information indicating, for example, a blood pressure, a pulse rate, a time, a name of a medical instrument, a name of a mode of the medical instrument, and the like. The imaging device 120 is a device that images the information displayed on the information providing device 100 in a case where the information providing device 100 cannot output the numerical information and the like to an external device and transmits the captured image data to the information drawing device 200. The imaging device 120 may be installed for each information providing device 100, and may provide the header information of the information imaged by each imaging device 120 to the information drawing device 200. In addition, the information providing device 100 is not limited to the above-described example.

The information drawing device 200 includes a controller 300 that controls each component, a light source 400 that irradiates drawing light, and an optical system 500 that scans the irradiation position of the drawing light from the light source 400. The controller 300 is an example of an information processing device and is realized by, for example, a central processing unit (CPU), a read only memory (ROM), a random access memory (RAM), and the like. In addition, the controller 300 may have an input from the manipulation unit 302 manipulated by the medical practitioner. The detailed configuration and processing of the controller 300 will be described later.

The light source 400 is a light source 400 that is controlled by the controller 300 and irradiates drawing light having illuminance visually recognizable under the light of the shadowless lamp 800. The light source 400 may be, for example, a laser source 400 using a semiconductor element. The laser source 400 using a semiconductor element may be, for example, a light source 400 that irradiates a red laser with a wavelength of about 610 nm to 780 nm, may be a light source 400 that irradiates a blue laser with a wavelength of about 430 nm to 460 nm, or may be a light source 400 that irradiates a green laser with a wavelength of about 500 nm to 570 nm. The laser source 400 using the semiconductor element as described above is generally used for a laser pointer or the like, and the laser source 400 using such a semiconductor element is used, so that the information drawing device 200 of the present embodiment is configured at a low cost with a small size.

In addition, with reference to the wavelength of the light source 400, it is considered that fatigue of the medical practitioner is less because red is a color that the medical practitioner is familiar with. In addition, since green is a color that is not present in the surgical field, there is an advantage that the contrast with the instruments present in the surroundings is high. In addition, the light source 400 may be a light source 400 which irradiates the drawing light having illuminance visually recognizable under the light of the shadowless lamp 800, and the configuration of the light source 400 is not particularly limited. In the information drawing system according to the present embodiment, the drawing light is scanned point by point by using the light source 400 as described above, so that information is displayed on the screen 600 at a higher illuminance than that of a display device such as a projector. As a result, the medical practitioner can visually recognize the information even under the shadowless lamp 800.

The optical system 500 is controlled by the controller 300 to be used to scan the reaching position of the drawing light irradiated from the light source 400 on the screen 600. In addition, the light source 400 and the optical system 500 may be referred to as a light irradiation unit 402. The detailed configuration of the light irradiation unit 402 is illustrated in FIG. 3.

Figure 3:
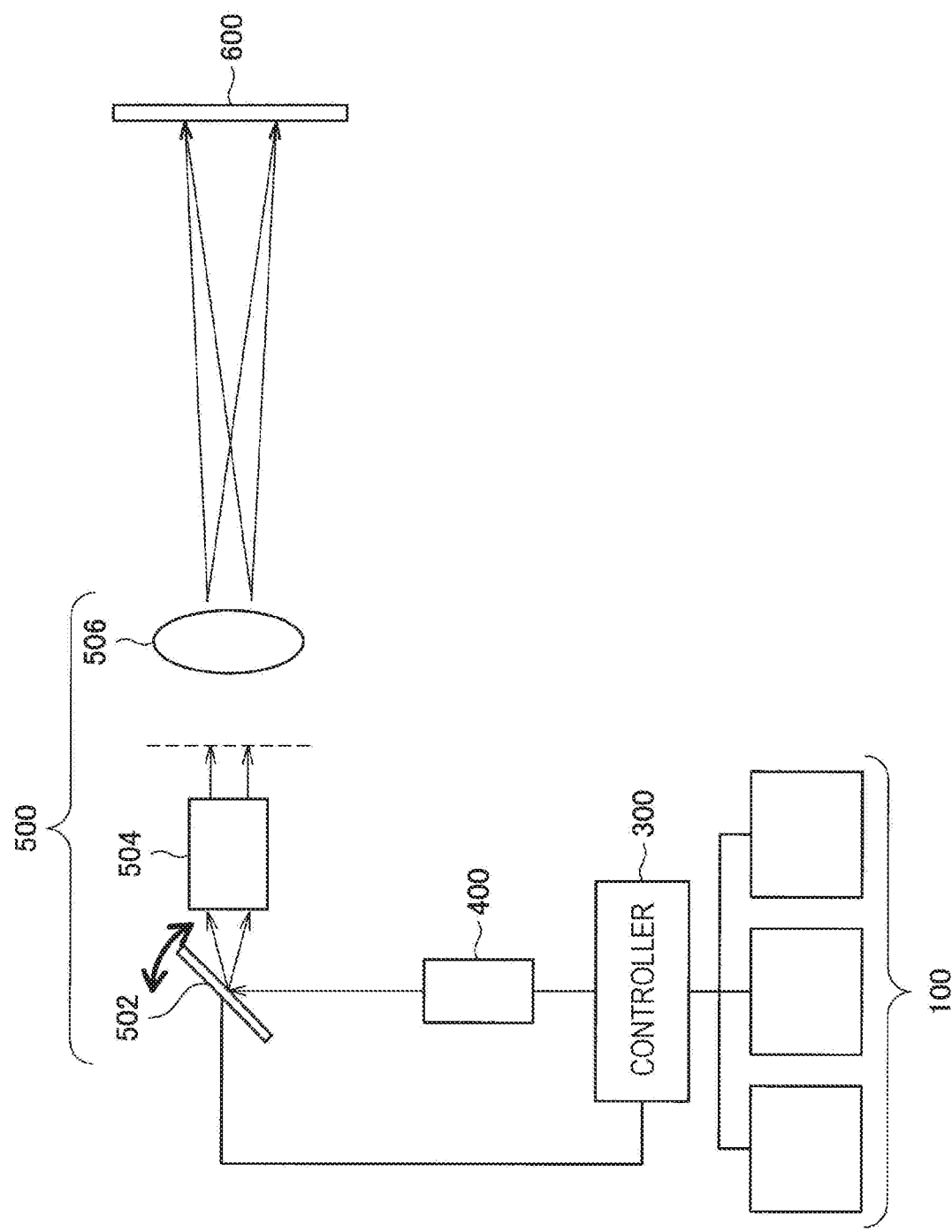
FIG. 3 is a diagram illustrating an example of a configuration of an information drawing system according to the embodiment of the present disclosure.

As illustrated in FIG. 3, the optical system 500 may include, for example, a scan mirror 502, a scan lens 504, and an imaging lens 506. In addition, the scan mirror 502 may be a two-dimensional micro electro mechanical system (MEMS) mirror, or two one-dimensional MEMS mirrors may be used.

As illustrated in FIG. 3, the scan mirror 502 is irradiated with the drawing light irradiated from the light source 400. The scan mirror 502 allows the drawing light irradiated from the light source 400 to be incident on the scan lens 504 as the operation state is controlled by the controller 300. The drawing light incident on the scan lens 504 is imaged on an image forming plane by the scan lens 504. Then, an image drawn by the drawing light imaged on the image forming plane is displayed on the screen 600 by the imaging lens 506.

In addition, instead of the MEMS mirror, a galvano mirror may be used as the scan mirror 502, and a vari-angle prism may be used as long as the scan mirror 502 is not driven. The vari-angle prism has a structure in which two sheets of glass are joined by a bellows including a film and the space between the two sheets of glass is filled with a transparent high refractive index liquid. In addition, the optical system 500 may be configured to scan the drawing light from the light source 400 on the screen 600, and the configuration of the optical system 500 is not particularly limited as described above. In addition, the information drawing device 200 may draw an image on the screen 600 by using the drawing light by directly moving the installation position of the light source 400 without the optical system 500.

<1-2. Configuration Example of Controller>

Figure 4:
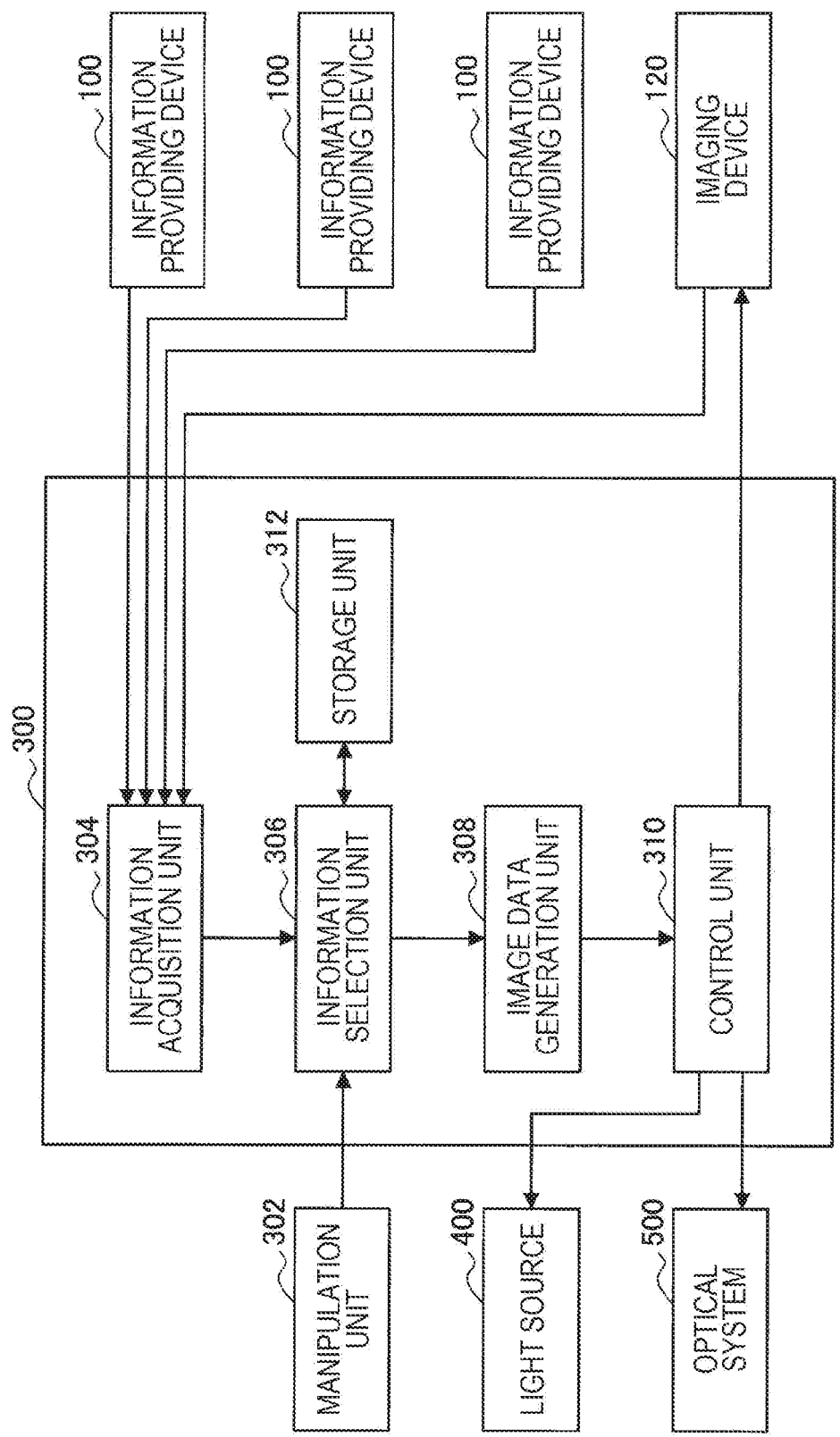
FIG. 4 is a block diagram illustrating an example of a configuration of a controller according to the embodiment of the present disclosure.

Heretofore, the overall configuration of the information drawing system according to the present embodiment has been described. Hereinafter, a configuration example of the controller 300 of the present embodiment is described. The controller 300 is a device for acquiring information from the information providing device 100 and controlling the light source 400 and the optical system 500. As illustrated in FIG. 4, the controller 300 includes an information acquisition unit 304, an information selection unit 306, an image data generation unit 308, a control unit 310, and a storage unit 312.

The information acquisition unit 304 acquires, from the plurality of information providing devices 100, numerical information such as biological information of the patient 18 or setting values of the medical instrument and header information indicating what kind of information the numerical information is. In addition, the information acquisition unit 304 may acquire a captured image from the imaging device 120 that images the information displayed on the information providing device 100. As described above, the imaging device 120 may be installed for each information providing device 100, and the information acquisition unit 304 may acquire header information of the information imaged by each imaging device 120 together with the captured image from the imaging device 120.

Figure 5:
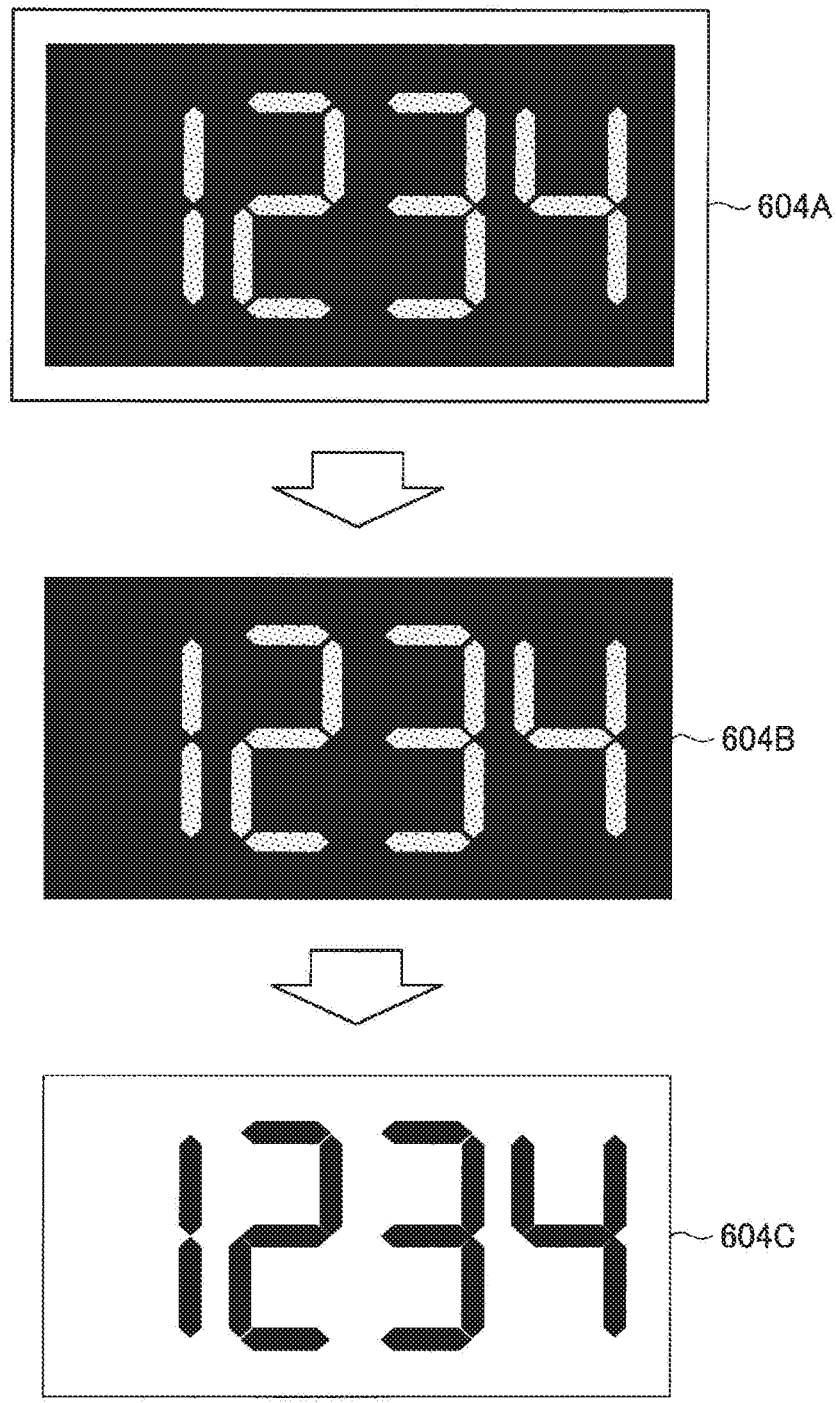
FIG. 5 is a diagram illustrating an example of an image processing method in an information acquisition unit of the embodiment of the present disclosure.

FIG. 5 is a diagram illustrating a method of processing the captured image from the imaging device 120 acquired by the information acquisition unit 304. Reference numeral 604A represents a captured image imaged by the imaging device 120, and the information acquisition unit 304 cuts out an image area, in which a numerical value is displayed as represented by 604B, from the captured image represented by 604A. Then, the information acquisition unit 304 performs contrast adjustment and binarization on the cut-out image. Next, the information acquisition unit 304 inverts the image processed in 604B as represented by 604C. The information acquisition unit 304 acquires information from the imaging device 120 by performing such image processing. Herein, since the information acquisition unit 304 does not perform character recognition based on the captured image, an incorrect numerical value is prevented from being presented to the medical practitioner. Providing incorrect information to the medical practitioner in a medical practice leads to medical errors, so that it is important to prevent misrecognition. However, since the current character recognition technology is highly developed, the probability of misrecognition is low, and in order to improve the degree of freedom of information processing, such as changing recognized character information into a more easily recognizable font, the information acquisition unit 304 may perform the character recognition process based on the captured image. In addition, the specific method of the character recognition process is not particularly limited and may be performed by a known technique such as edge detection, for example, in the related art.

Returning to FIG. 4, the information acquisition unit 304 transmits, to the information selection unit 306, the numerical information and the header information acquired directly from the information providing device 100 or acquired from the imaging device 120 as described above. The information selection unit 306 selects the numerical information to be drawn by the drawing light from among the plurality of pieces of numerical information received from the information acquisition unit 304 on the basis of the received header information. The information selection unit 306 may select the information according to the output from the manipulation unit 302 manipulated by the medical practitioner and may select the information on the basis of the database where the medical practice stored in the storage unit 312 and the information to be selected are associated with each other, as described later.

The information selection unit 306 selects the information in this manner, so that the information to be recognized by the medical practitioner according to the situation is presented to the medical practitioner. Even if a lot of information is presented to the medical practitioner during the medical practice, it is difficult to distinguish which information is important information, and thus, selection of the information to the presented by the information selection unit 306 is useful for the medical practitioner to reliably recognize important information. In addition, in a case where a large amount of information is presented to the medical practitioner without being selected, the medical practitioner may misrecognize the information, which leads to the medical errors, and thus, it is preferable that such misrecognition of the information is prevented. From this point of view, it is useful that the information to be presented to the medical practitioner is selected by the information selection unit 306.

Here, the manipulation unit 302 may be a foot pedal or may be a voice recognition unit that recognizes a voice of the medical practitioner and outputs information to be selected. The medical practitioner can reliably select the information by using the foot pedal, and due to voice recognition, the medical practitioner can select the information without moving the body. As described above, the fact that information can be reliably selected is useful for preventing misrecognizing of the information by the medical practitioner, and the fact that information can be selected without moving the body is useful in a medical site (particularly during surgery) where even fine body movements lead to medical errors. Note that the manipulation unit 302 may have any configuration as long as the medical practitioner can select information, and the configuration is not particularly limited.

The image data generation unit 308 generates image data to be drawn by using the drawing light irradiated from the light source 400 on the basis of the information selected by the information selection unit 306. For example, in a case where the information selected by the information selection unit 306 is a setting value of the coagulation mode of the electric knife, image data such as "Power Co 1234" is generated. Herein, "Power Co" is information indicating a setting value of the coagulation mode of the electric knife and is generated on the basis of the header information. In addition, "1234" is generated on the basis of numerical information acquired from a control device of an electric knife that is one of the information providing devices 100.

The control unit 310 controls each component of the information drawing device 200 and may be configured with, for example, a CPU, a ROM, or a RAM. As illustrated in FIG. 4, the control unit 310 may control the imaging device 120, the light source 400, and the optical system 500. The control unit 310 controls the light source 400 and the optical system 500 so that an image based on the image data received from the image data generation unit 308 is drawn on the screen 600 by the drawing light.

Figure 6:
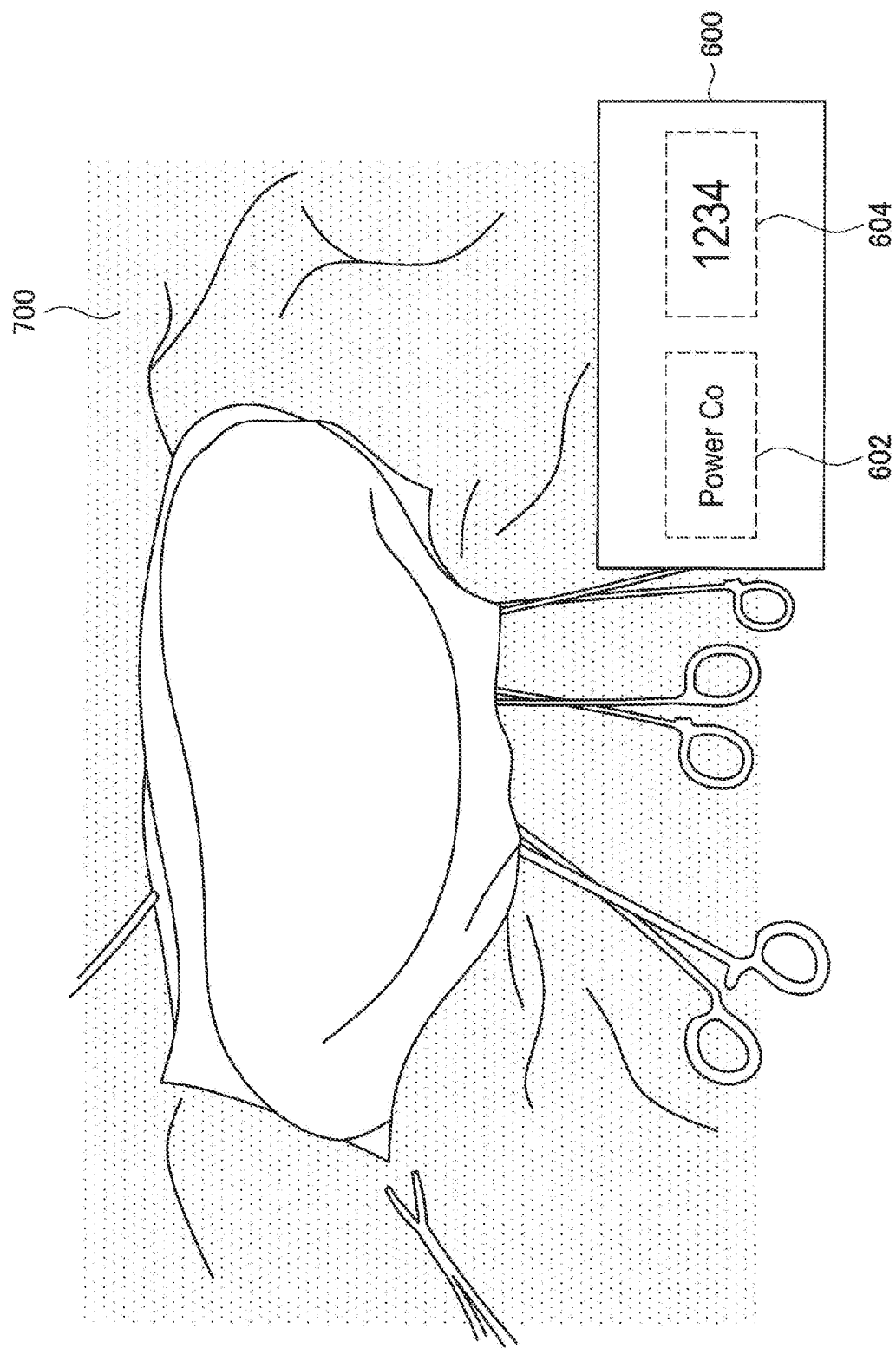
FIG. 6 is a diagram illustrating an example of an information displaying method in the embodiment of the present disclosure.

FIG. 6 is a diagram illustrating a state where information is presented by the information drawing system described above. In FIG. 6, the image generated by the above-described image data generation unit 308 is drawn by the drawing light on the screen 600 installed on the drape 700 near the surgical site. As can be understood from FIG. 6, on the screen 600, the header information is displayed in the header information display area 602, and the numerical information related to the header information is displayed in the numerical information display area 604. Thus, the medical practitioner can check the information without checking the numerical information and the like from the assistant by the information being presented near the surgical site so as to be visually recognized under the light of the shadowless lamp 800. This allows the medical practitioner to proceed with the medical practice without time loss. In addition, misrecognition caused by the medical practitioner mishearing the information aurally notified by the assistant can be prevented.

<1-3. Processing Example of Controller>

Figures 7, 8:
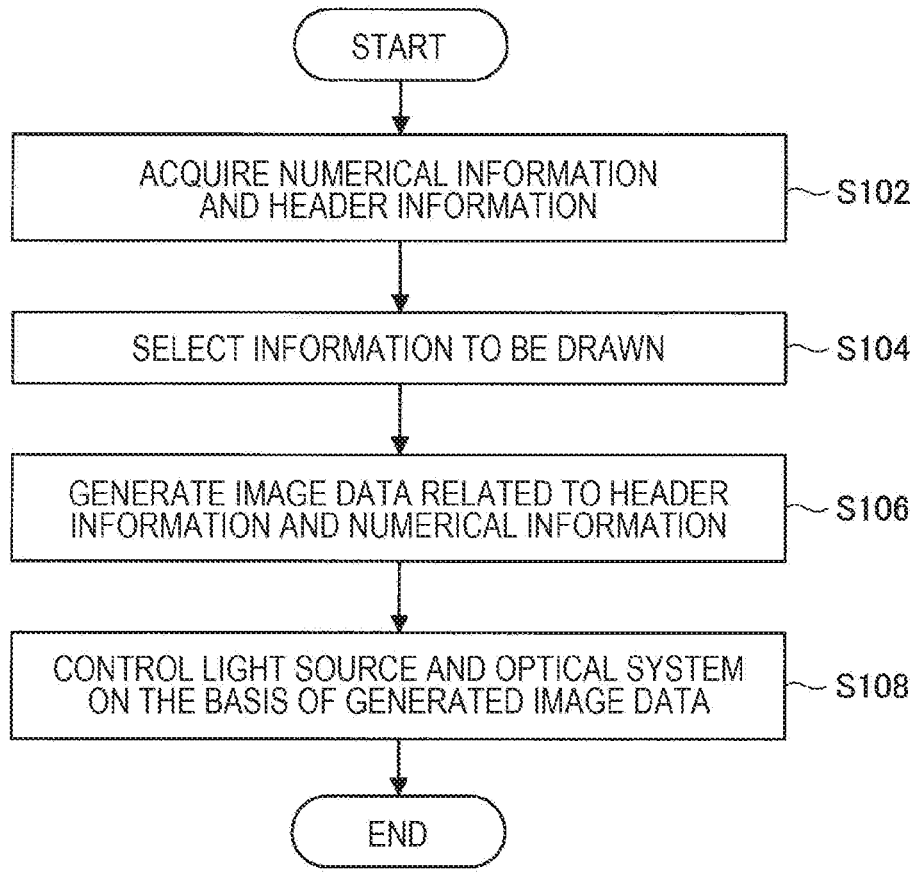
FIG. 7 is a flowchart illustrating an example of processing in the controller of the embodiment of the present disclosure.
FIG. 8 is a diagram illustrating an example of a database stored in a storage unit of the embodiment of the present disclosure.

Heretofore, the configuration of the controller 300 has been described. Hereinafter, a processing example performed by the controller 300 will be described. FIG. 7 is a flowchart illustrating basic processes executed by controller 300.

First, in S102, the information acquisition unit 304 acquires numerical information and header information indicating the type of the numerical information from a plurality of the information providing devices 100 or a plurality of the imaging devices 120. Next, in S104, the information selection unit 306 receives the numerical information and the header information from the information acquisition unit 304 and selects the information to be presented to the medical practitioner on the basis of the output from the manipulation unit 302 or on the basis of the database stored in the storage unit 312. The process in which the information selection unit 306 selects the information on the basis of the database stored in the storage unit 312 will be described later.

Next, in step S106, the image data generation unit 308 generates image data related to the header information and the numerical information on the basis of the information selected by the information selection unit 306. Then, in step S108, the control unit 310 controls the light source 400 and the optical system 500 so as to draw the image data generated by the image data generation unit 308.

Heretofore, the basic processing example executed in the controller 300 has been described. Herein, in S104 of FIG. 7, the process of selecting the information on the basis of the database stored in the storage unit 312 by the information selection unit 306 will be described. FIG. 8 is a diagram illustrating an example of a database in which the medical practice and the information to be selected, which is stored in the storage unit 312, are associated with each other.

For example, the medical practice performed by the medical practitioner may be a medical practice such as "incision", "arterial blockade", or "closing stomach" as illustrated in FIG. 8, and the information to be selected may be associated with each medical practice. For example, when the "incision" is performed, the amount of bleeding and the setting value of the electric knife are important information, so that the "amount of bleeding" and the "setting value of the electric knife" as the information to be selected may be associated with the "incision". Similarly, in the case of the "arterial blockade" which is a medical practice, since the elapsed time from the arterial blockade is important information, the "elapsed time from the arterial blockade" as the information to be selected may be associated. Moreover, in the case of the "closing stomach" which is a medical practice, since the used gauze should not remain in the abdomen, the "number of gauze sheets" as the information to be selected may be associated.

In addition, the information drawing system according to the present embodiment can be used for various types of surgery such as respiratory surgery, liver surgery, digestive tract surgery, cardiovascular surgery, and brain surgery. Thus, for example, in the database, a surgical technique which is an example of a medical practice and information to be selected may be associated with each other. For example, since respiratory surgery and liver surgery are surgeries on portions with large blood vessels, management of the amount of bleeding is important. Therefore, in the database, the "respiratory surgery" and the "liver surgery" as medical practices may be associated with the "amount of bleeding" as the information to be selected. In addition, in the cardiovascular surgery and the brain surgery, since the setting value of the electric knife is frequently changed, the setting value of the electric knife is important information. Therefore, in the database, the "cardiovascular surgery" and the "brain surgery" as medical practices may be associated with the "setting value of the electric knife" as the information to be selected.

As described above, the information selection unit 306 selects the information to be presented to the medical practitioner on the basis of the database in which the medical practice and the information to be selected are associated with each other. For example, if the information selection unit 306 determines from the operation state of the information providing device 100 that the "incision" is being performed, the "amount of bleeding" and/or the "setting value of the electric knife" is selected as the information to be presented to the medical practitioner. In addition, the information selection unit 306 may estimate what kind of medical practice is being performed on the basis of the information from the voice recognition unit. For example, if the word "incision" is detected in a conversation more than a predetermined frequency, the information selection unit 306 estimates that the "incision" is being performed, and the information to be presented to the medical practitioner may be selected on the basis of the database. The information selection unit 306 may also estimate the medical practice being performed on the basis of the elapsed time after the medical practice (for example, surgical operation) is started.

In addition, in the database, steps in each medical practice may be associated with the information to be selected. For example, in a case where a surgical operation including the steps of "opening stomach", "arterial blockade", and "closing stomach" is performed as a medical practice, the information corresponding to each step is selected. That is, in the step of opening stomach in the surgery involved with arterial blockade, the "amount of bleeding" or the "setting value of the electric knife" is selected as the information to be presented. In addition, in the step of arterial blockade, the "elapsed time from arterial blockade" is selected as the information to be presented. In the step of closing stomach, the "number of gauze sheets" is selected as the information to be presented. Thus, each step in the medical practice and the selected information are associated with each other, so that information that is important in each step of the medical practice is appropriately selected and presented to the medical practitioner. Accordingly, the medical practitioner can easily recognize the appropriate information at an appropriate timing.

Figure 9:
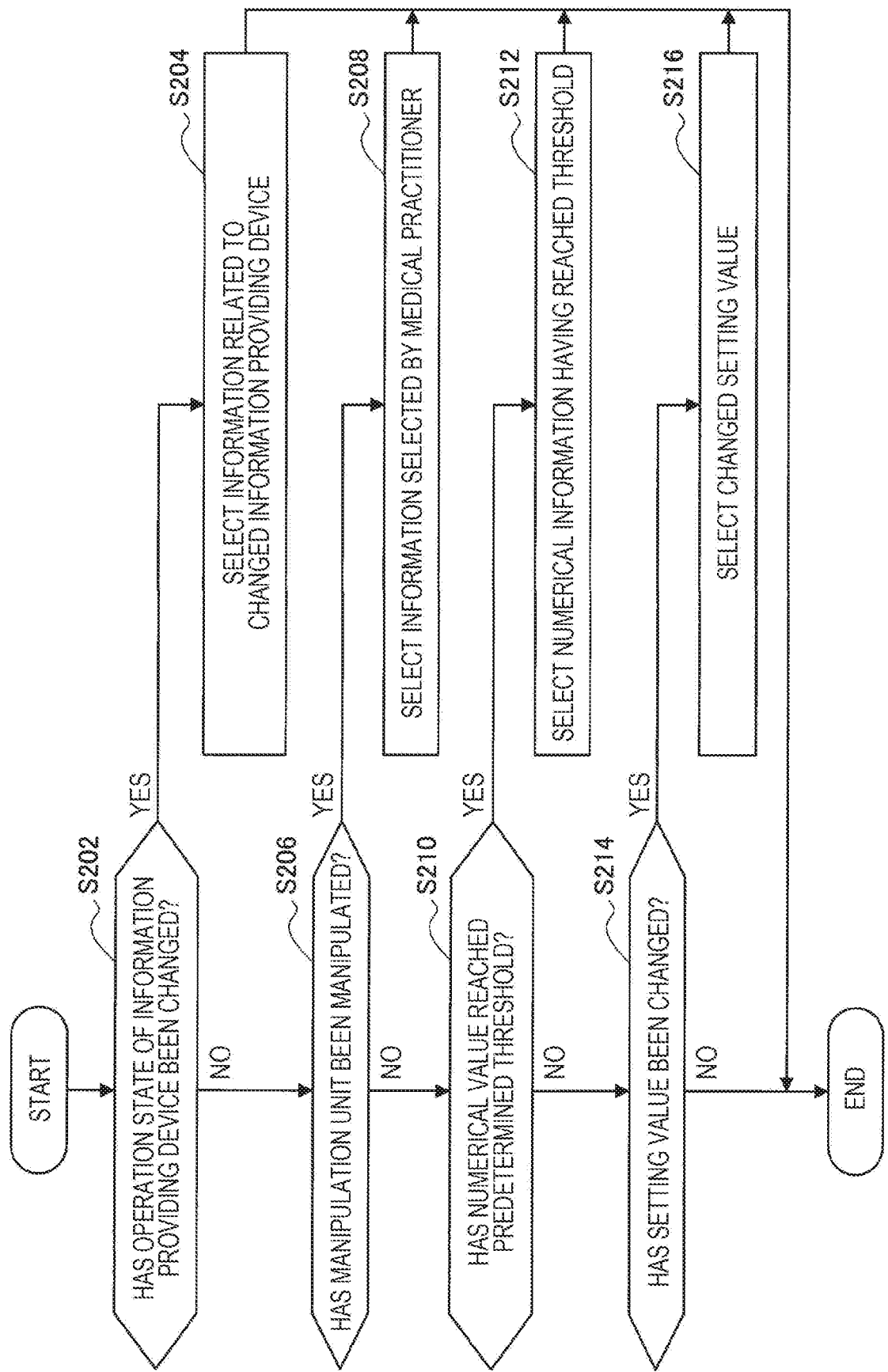
FIG. 9 is a flowchart illustrating an example of processing in the controller of the embodiment of the present disclosure.

Heretofore, the database stored in the storage unit 312 and the process of selecting the information by the information selection unit 306 by using the database have been described. Next, FIG. 9 illustrates an example of a process in which the information selection unit 306 selects the information to be presented to the medical practitioner on the basis of various information. For example, in S202, the information selection unit 306 determines whether or not the operation state of the information providing device 100 has been changed. Herein, for example, the information selection unit 306 may detect that the power of the information providing device 100 is turned on or may detect that the operation mode of the information providing device 100 is changed. When it is detected in S202 that the operation state of the information providing device 100 has been changed, the information selection unit 306 selects information related to the information providing device 100 in which the operation state has been changed in S204.

Next, in S206, the information selection unit 306 determines whether or not the manipulation unit 302 has been manipulated by the medical practitioner. When it is detected in S206 that the manipulation unit 302 has been manipulated by the medical practitioner, the information selection unit 306 selects information on the basis of the output from the manipulation unit 302 (S208).

Next, in S210, the information selection unit 306 determines whether or not predetermined numerical information acquired from the information providing device 100 has reached a predetermined threshold. Herein, for example, the information selection unit 306 may detect that the amount of bleeding has reached a predetermined threshold. When it is detected in S210 that the predetermined numerical information acquired from the information providing device 100 has reached a predetermined threshold, the information selection unit 306 selects the information having reached the predetermined threshold in S212.

Next, in S214, the information selection unit 306 determines whether or not the setting value of the information providing device 100 has been changed. Herein, for example, the information selection unit 306 may detect that the setting value of the electric knife has been changed. When it is detected in S214 that the setting value of the information providing device 100 has been changed, the information selection unit 306 selects the changed setting value in S216. As described above, the information selection unit 306 selects the information to be drawn on the basis of various information. By being configured in this manner, the information drawing device 200 according to the present embodiment can present information suitable for the timing to the medical practitioner at various timings.

2. Screen

Heretofore, the configuration of the information drawing device 200 according to the present embodiment has been described. Hereinafter, the configuration of the screen 600 used in the present embodiment will be described. As described above, since the information drawing device 200 according to the present embodiment is used under the shadowless lamp 800, the drawing light having illuminance visually recognizable under the light of the shadowless lamp 800 is used. In the information drawing device 200 in which such drawing light is used, the screen 600 absorbing the light of the shadowless lamp 800 and having a relatively high reflectance for the wavelength of the drawing light is used, so that the medical practitioner can more easily visually recognize the information to be presented. Therefore, in the present embodiment, the screen 600 including a layer that absorbs the light of the shadowless lamp 800 and a layer having a relatively high reflectance for the wavelength of the drawing light is used.

Figure 10:
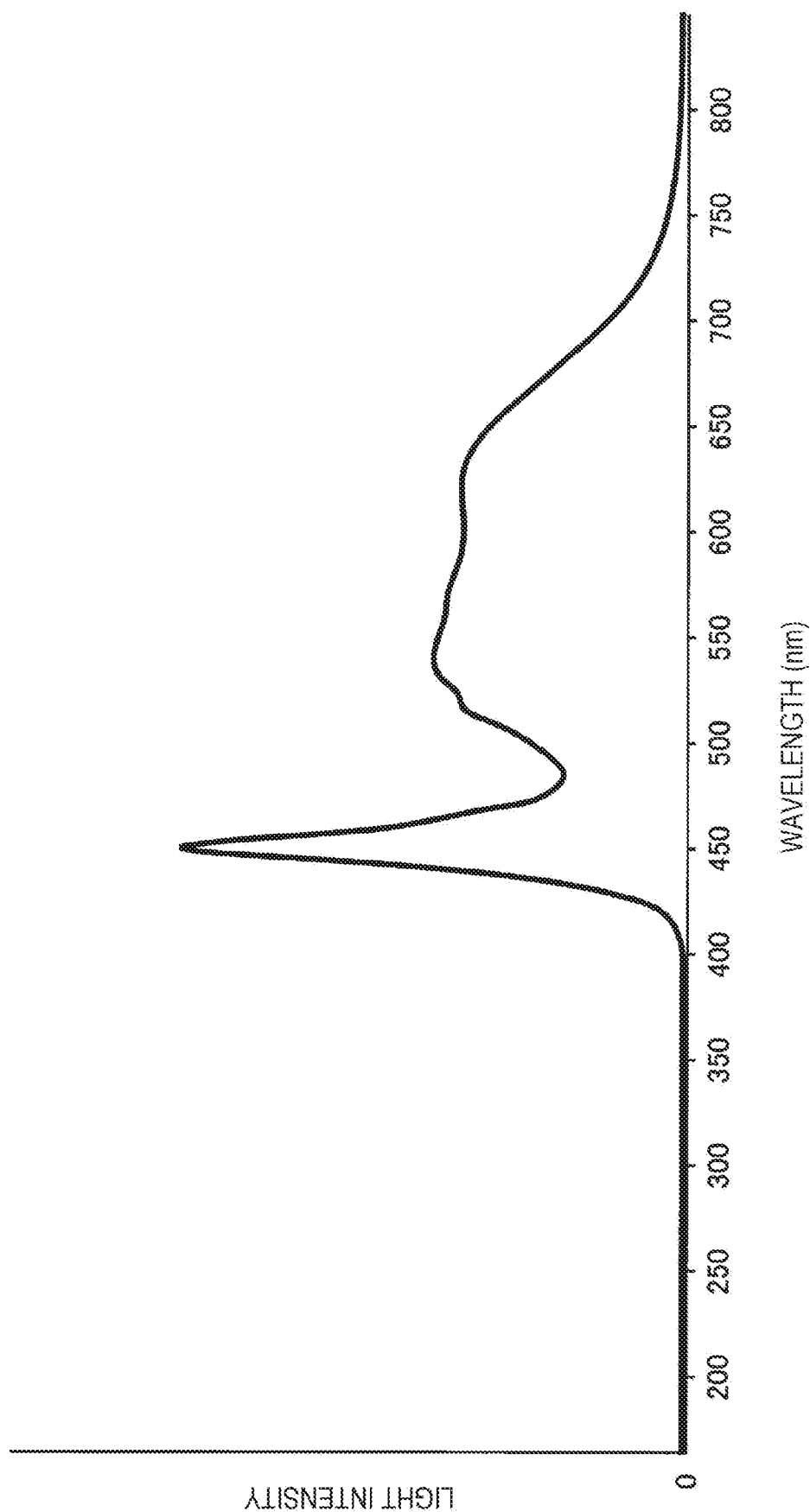
FIG. 10 is a graph illustrating an example of a spectrum of a shadowless lamp.

In order to describe the characteristics of the screen 600, the wavelength spectrum of the shadowless lamp 800 will first be described. FIG. 10 is a graph illustrating the spectrum of the shadowless lamp 800 employing a light emitting diode (LED) as a light source. In the spectrum of the shadowless lamp 800 illustrated in FIG. 10, the light intensity of the wavelength near 450 nm and the light intensity of the wavelength near 540 to 650 nm become strong, while the light intensity of the wavelength of 480 to 490 nm is weak. Therefore, for the shadowless lamp 800 having such a spectrum, the light having a wavelength of 480 to 490 nm is preferably used as the drawing light. In addition, it is preferable that the screen 600 has a relatively high reflectance for the light having a wavelength of 480 to 490 nm as compared with the light having other wavelengths.

Figure 11:
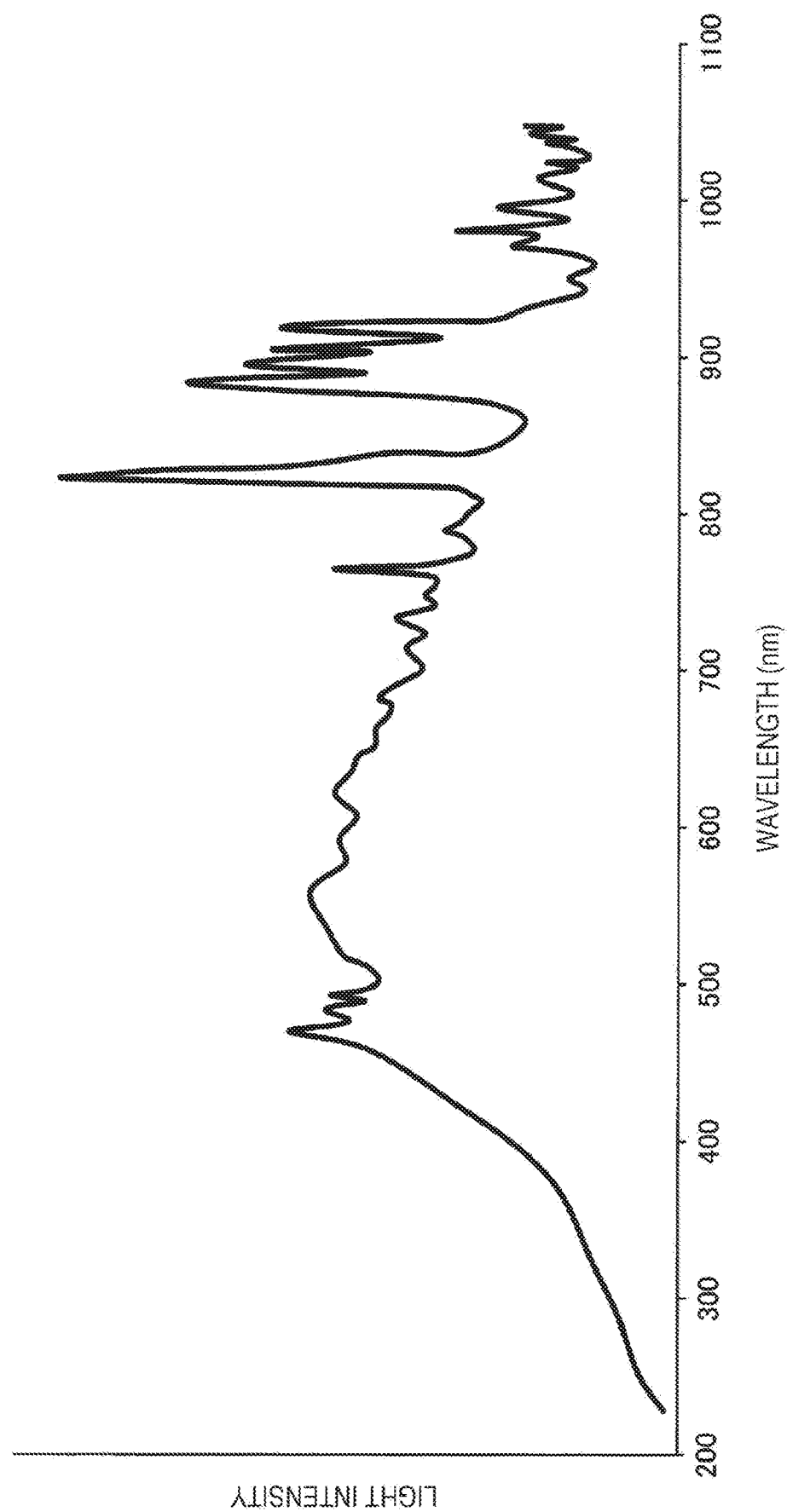
FIG. 11 is a graph illustrating an example of a spectrum of a shadowless lamp.

Next, FIG. 11 is a graph illustrating the spectrum of the shadowless lamp 800 employing a xenon lamp as a light source. In the spectrum of the shadowless lamp 800 illustrated in FIG. 11, there is no particular wavelength range where the light intensity becomes weak. However, even in a situation where the shadowless lamp 800 having such a spectrum is used, the screen 600 selectively reflects the wavelength of the drawing light and absorbing the light of other wavelengths, so that the medical practitioner can easily visually recognize the information displayed on the screen 600.

<2-1. Configuration of Screen>

Figure 12:
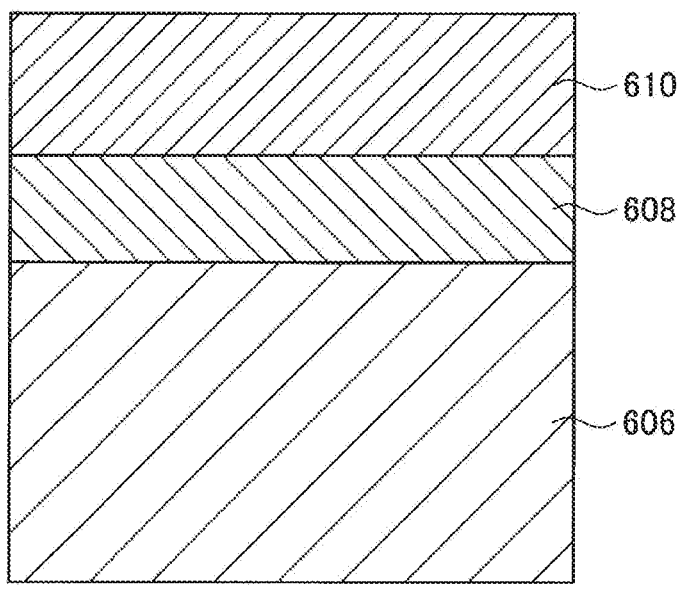
FIG. 12 is a diagram illustrating an example of a configuration of a screen of the embodiment of the present disclosure.

FIG. 12 is a diagram illustrating an example of a configuration of the screen 600 of the present embodiment. As illustrated in FIG. 12, the screen 600 of the present embodiment is configured with a substrate 606, a light absorption layer 608, and a selective reflection layer 610. For example, aluminum may be used for the substrate 606, and black alumite processing is performed on the top of the substrate as the light absorption layer 608. Herein, the refractive index n of the black alumite is 1.7. In addition, on the light absorption layer 608, the selective reflection layer 610 which selectively reflects the wavelength of the drawing light is formed as described above. The configuration of the selective reflection layer 610 will be described in detail below.

Figure 13:
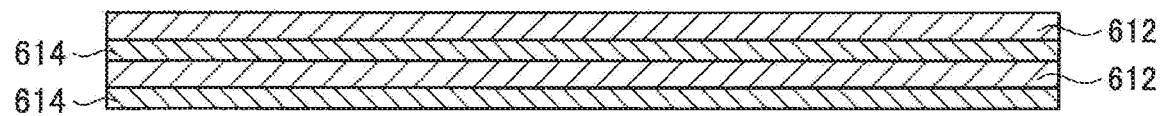
FIG. 13 is a diagram illustrating an example of a configuration of a selective reflection layer of the screen of the embodiment of the present disclosure.

FIG. 13 is a diagram illustrating an example of the configuration of the selective reflection layer 610 formed on the screen 600 of the present embodiment. The selective reflection layer 610 is configured with a multilayer film in which a high refractive index film 612 and a low refractive index film 614 having a refractive index lower than that of the high refractive index film 612 are alternately stacked. Herein, for example, tantalum pentoxide ($Ta_2O_5$) having a refractive index n of 2.0 may be used for the high refractive index film 612, and for example, silicon dioxide ($SiO_2$) having a refractive index n of 1.47 may be used for the low refractive index film 614. In addition, in FIG. 13, the selective reflection layer 610 formed by alternately stacking the total of four layers of the high refractive index film 612 and the low refractive index film 614 will be described.

Assuming that the drawing light of 640 nm is used in the information drawing system according to the present embodiment, for example, the film thickness Z1 of the high refractive index film 612 is preferably 256 nm (Z1=640 nm/2×0.80), and the film thickness Z2 of the low refractive index film 614 is preferably 261 nm (Z2=640 nm/1.47×0.60).

Figure 14:
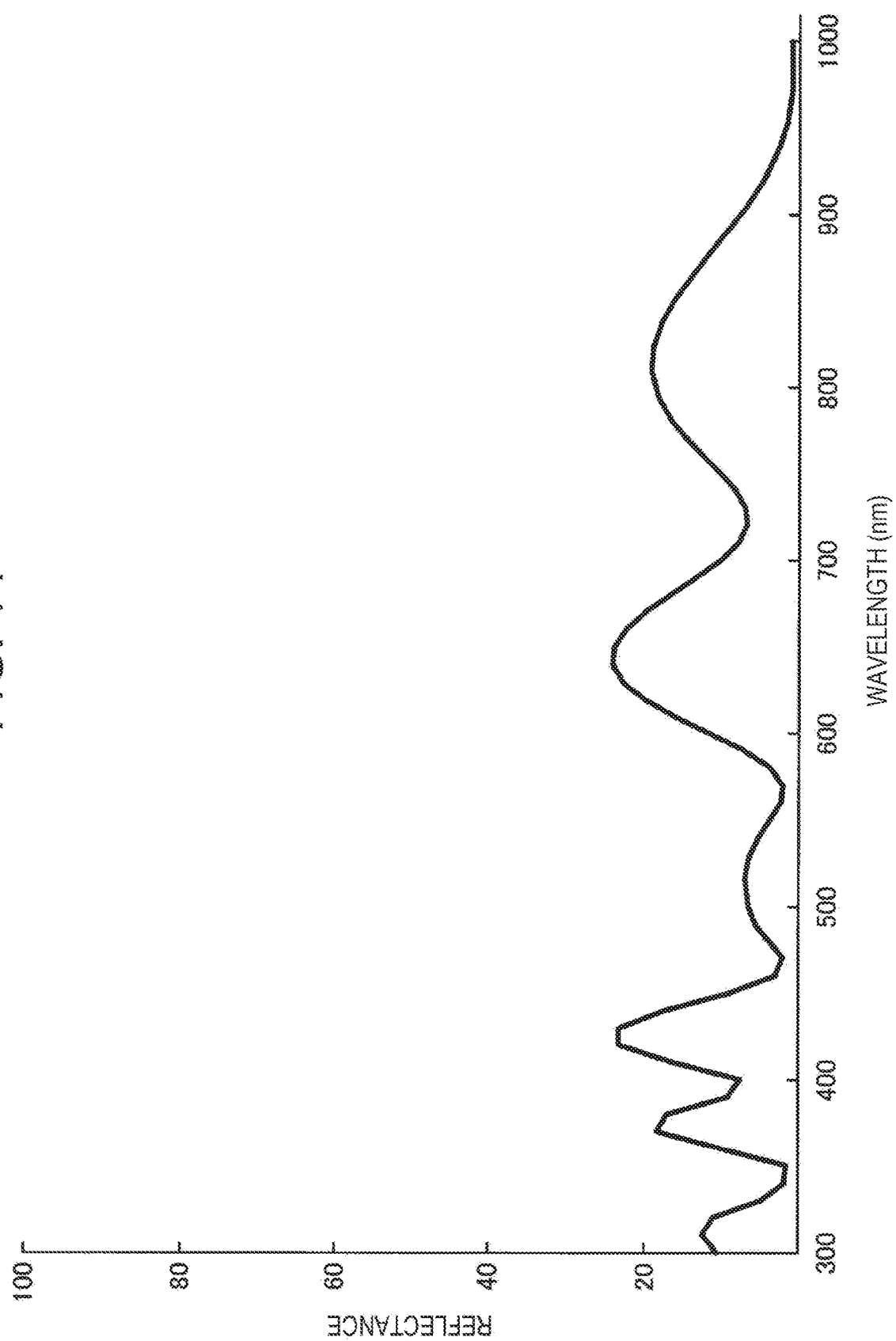
FIG. 14 is a graph illustrating an example of reflectance characteristics of the selective reflection layer of the screen of the embodiment of the present disclosure.

FIG. 14 is a graph illustrating the reflectance of the selective reflection layer 610 illustrated in FIG. 13. As can be understood from FIG. 14, the configuration of the selective reflection layer 610 illustrated in FIG. 13 has a reflectance (reflectance of 24.2%) for the wavelength of 640 nm which is the wavelength of the drawing light, which is higher than a reflectance for the other wavelengths.

Figure 15:
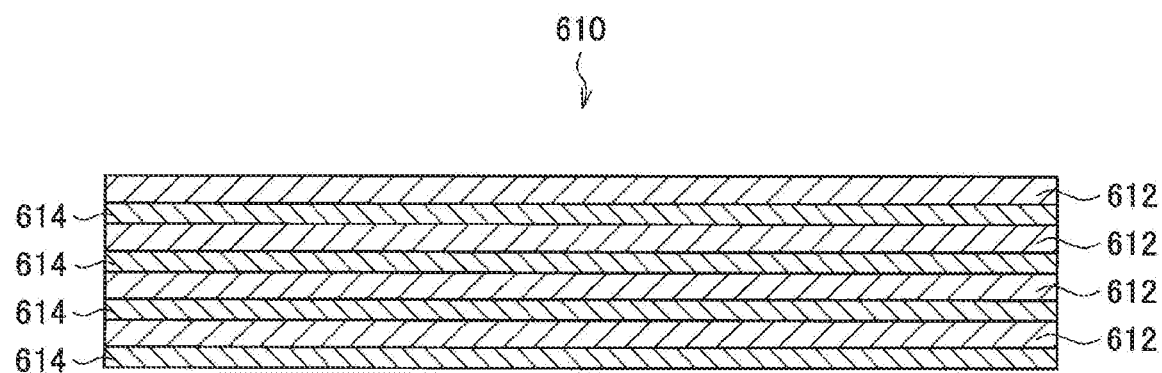
FIG. 15 is a diagram illustrating an example of the configuration of the selective reflection layer of the screen of the embodiment of the present disclosure.

Next, FIG. 15 is a diagram illustrating another example of the configuration of the selective reflection layer 610 illustrated in FIG. 13. Herein, in the example of the selective reflection layer 610 illustrated in FIG. 15, similarly to the selective reflection layer 610 illustrated in FIG. 13, tantalum pentoxide ($Ta_2O_5$) is used for the high refractive index film 612, and silicon dioxide ($SiO_2$) is used for the low refractive index film 614. In addition, in FIG. 15, the selective reflection layer 610 formed by alternately stacking the total of eight layers of the high refractive index film 612 and the low refractive index film 614 will be described.

In the selective reflection layer 610 illustrated in FIG. 15, assuming that the drawing light of 640 nm is used as described above, the film thickness Z1 of the high refractive index film 612 is preferably 272 nm (Z1=640 nm/2×0.85), and the film thickness Z2 of the low refractive index film 614 is preferably 279 nm (Z2=640 nm/1.47×0.64).

Figure 16:
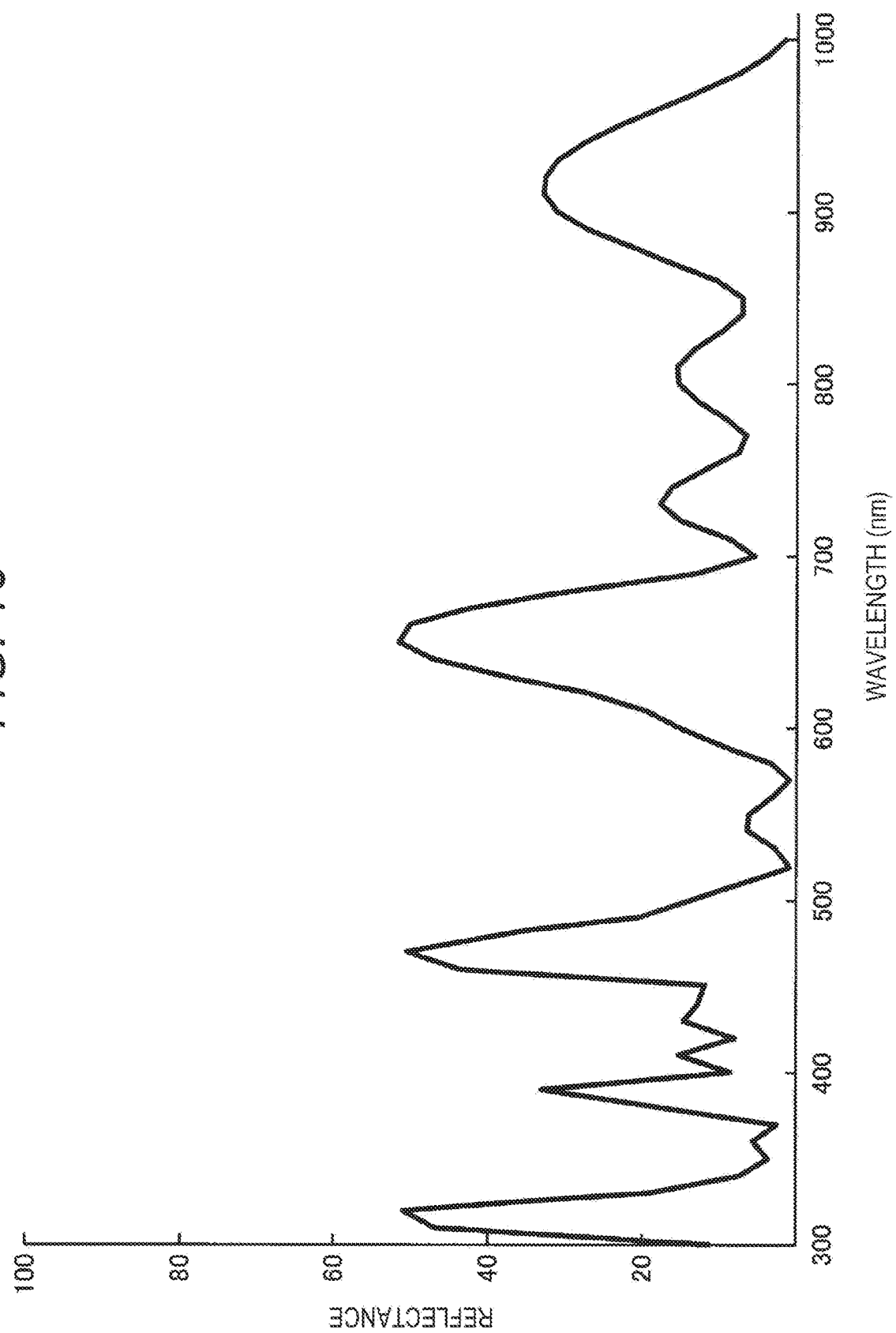
FIG. 16 is a graph illustrating an example of the reflectance characteristics of the selective reflection layer of the screen of the embodiment of the present disclosure.

FIG. 16 is a graph illustrating the reflectance of the selective reflection layer 610 illustrated in FIG. 15. As can be understood from FIG. 16, the configuration of the selective reflection layer 610 illustrated in FIG. 15 has a reflectance (reflectance of 47.5%) for the wavelength of 640 nm which is the wavelength of the drawing light, which is higher than a reflectance for the other wavelengths. In addition, it can be understood that the reflectance (47.5%) for the wavelength (640 nm) of the drawing light in the graph illustrated in FIG. 16 is higher than the reflectance (24.2%) for the wavelength (640 nm) of the drawing light illustrated in FIG. 14.

Figure 17:
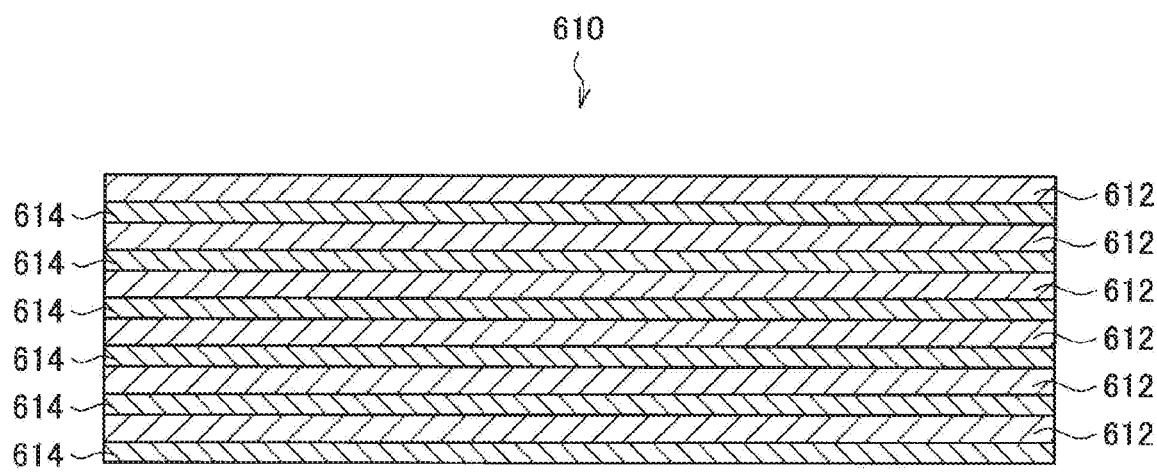
FIG. 17 is a diagram illustrating an example of the configuration of the selective reflection layer of the screen of the embodiment of the present disclosure.

FIG. 17 is a diagram illustrating another example of the configuration of the selective reflection layer 610 illustrated in FIGS. 13 and 15. Herein, in the example of the selective reflection layer 610 illustrated in FIG. 17, similarly to the selective reflection layer 610 illustrated in FIGS. 13 and 15, tantalum pentoxide ($Ta_2O_5$) is used for the high refractive index film 612, and silicon dioxide ($SiO_2$) is used for the low refractive index film 614. In addition, in FIG. 17, the selective reflection layer 610 formed by alternately stacking twelve layers of the high refractive index film 612 and the low refractive index film 614 will be described.

In the selective reflection layer 610 illustrated in FIG. 17, assuming that the drawing light of 640 nm is used as described above, similarly to the configuration of the selective reflection layer 610 illustrated in FIG. 15, the film thickness Z1 of the high refractive index film 612 is preferably 272 nm (Z1=640 nm/2×0.85), and the film thickness Z2 of the low refractive index film 614 is preferably 279 nm (Z2=640 nm/1.47×0.64).

Figure 18:
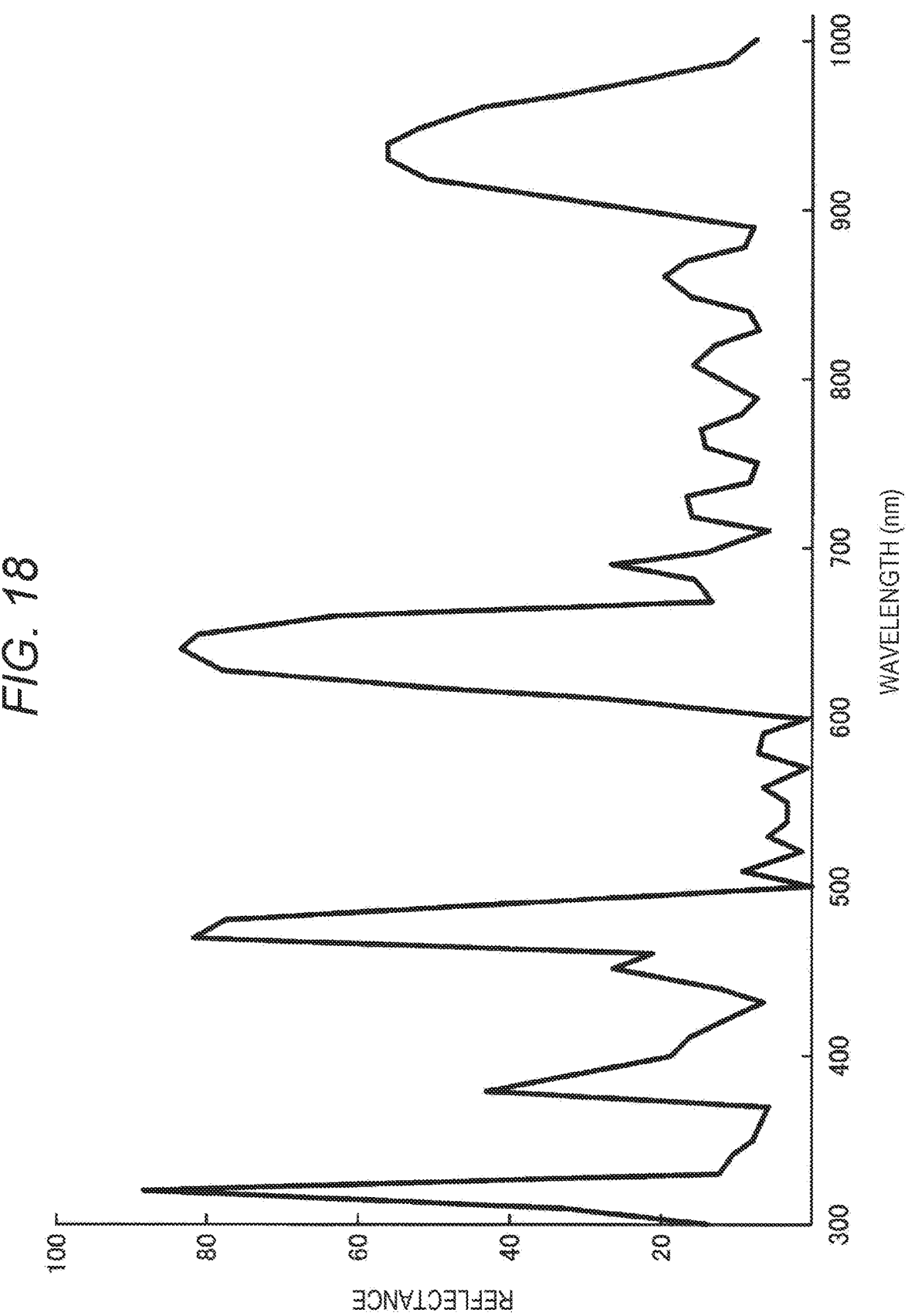
FIG. 18 is a graph illustrating an example of the reflectance characteristics of the selective reflection layer of the screen of the embodiment of the present disclosure.

FIG. 18 is a graph illustrating the reflectance of the selective reflection layer 610 illustrated in FIG. 17. As can be understood from FIG. 18, the configuration of the selective reflection layer 610 illustrated in FIG. 17 has a reflectance (reflectance of 84%) for the wavelength of 640 nm which is the wavelength of the drawing light, which is higher than a reflectance for the other wavelengths. In addition, it can be understood that the reflectance (84%) for the wavelength (640 nm) of the drawing light in the graph illustrated in FIG. 18 is higher than the reflectance (47.5%) for the wavelength (640 nm) of the drawing light illustrated in FIG. 16.

In addition, the light having a wavelength (for example, a wavelength of about 450 nm and a wavelength of 500 nm to 600 nm) having a low reflectance in the selective reflection layer 610 described above reaches the light absorption layer 608 to be absorbed. On the other hand, as described above, since the reflectance of the light having a wavelength of 640 nm (that is, a wavelength of a red laser pointer) is high, the light having the wavelength is reflected without reaching the light absorption layer 608. Therefore, by using the screen 600 having the configuration as described above in the information drawing system according to the present embodiment, the drawing light is reflected at a higher intensity than the light having other wavelengths, so that the medical practitioner can more easily visually recognize the information presented by the drawing light. In addition, since the light having a wavelength having a low reflectance in the selective reflection layer 610 is absorbed by the light absorption layer 608, the medical practitioner can more easily visually recognize the information presented by the drawing light.

<2-2. Installation Method of Screen>

Figure 19:
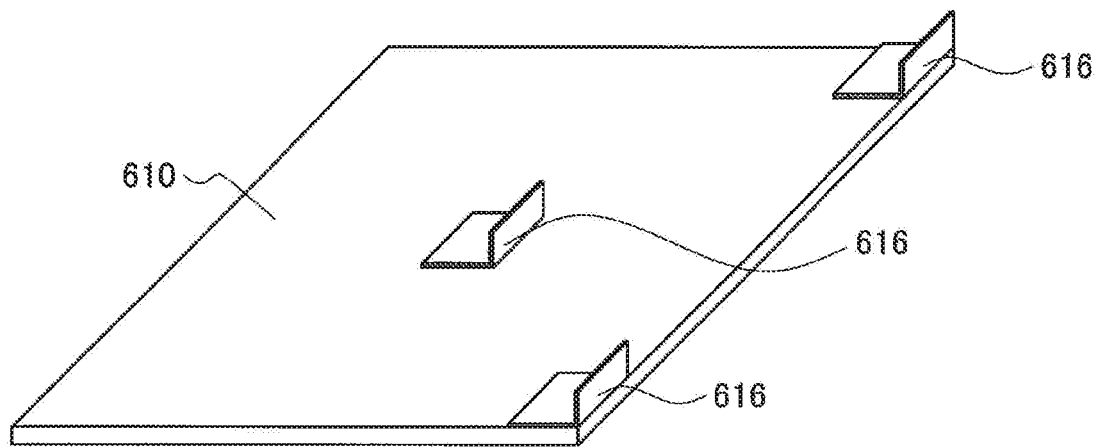
FIG. 19 is a diagram illustrating an example of a holder provided on the screen of the embodiment of the present disclosure.

Heretofore, the configuration of the screen 600 used in the information drawing device 200 according to the present embodiment has been described. Hereinafter, the installation method of the screen 600 used in the present embodiment is described. FIG. 19 is a diagram illustrating the opposite side of the surface on which the selective reflection layer 610 of the screen 600 is formed, that is, the back side of the substrate 606 of the screen 600. As illustrated in FIG. 19, the back side of the screen 600 is provided with a holder 616 used to place the screen 600 within the field of view of the medical practitioner.

The holder 616 is fixed to the drape 700 with the holder together with, for example, the drape 700 being pinched by an instrument such as a forceps. In addition, as illustrated in FIG. 19, the holder 616 is configured with a component which erects by bending a bendable thin member or an erecting member so as to facilitate fixation to the drape 700 or the like.

Figure 20:
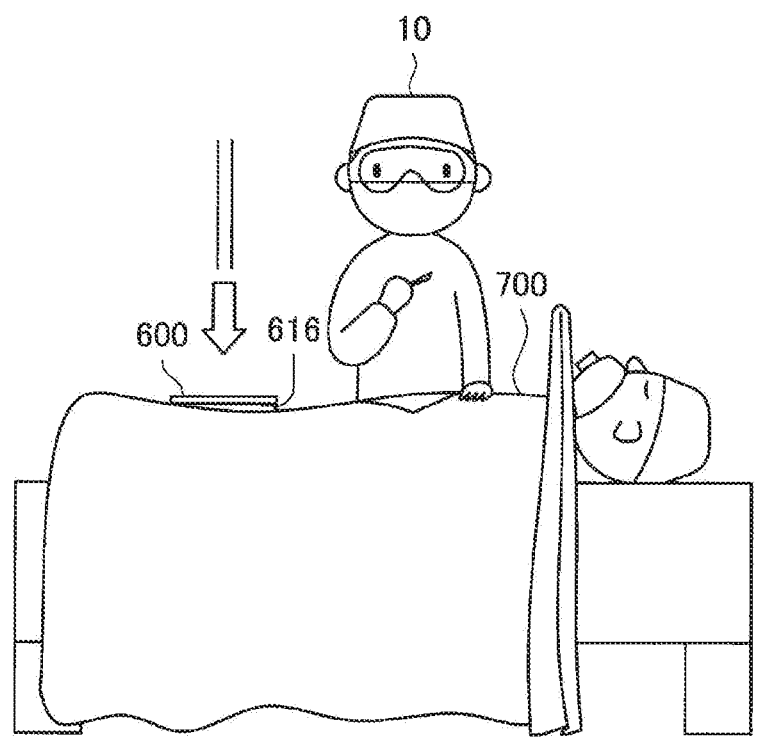
FIG. 20 is a diagram illustrating an installation example of the screen of the embodiment of the present disclosure.

FIG. 20 is a diagram illustrating a state of the screen 600 illustrated in FIG. 19 fixed to the drape 700. As described above, the screen 600 is fixed to the drape 700 with the holder 616 together with the drape 700 being pinched by an instrument such as forceps. In addition, as illustrated by an arrow in FIG. 20, the drawing light is irradiated from a position above the screen 600, and the drawing light draws the information to be grasped by the medical practitioner on the screen 600. The screen 600 is installed in this manner, and thus the operator 10 who is a medical practitioner can visually recognize quantitative numerical values such as a setting value of a device, a blood pressure value, and an amount of bleeding without looking away from the surgical field. In addition, it is preferable that the screen 600 is installed on the opposite side of the hand of the operator 10 holding the medical instrument so as not to interfere with the procedure of the operator 10.

Figure 21:
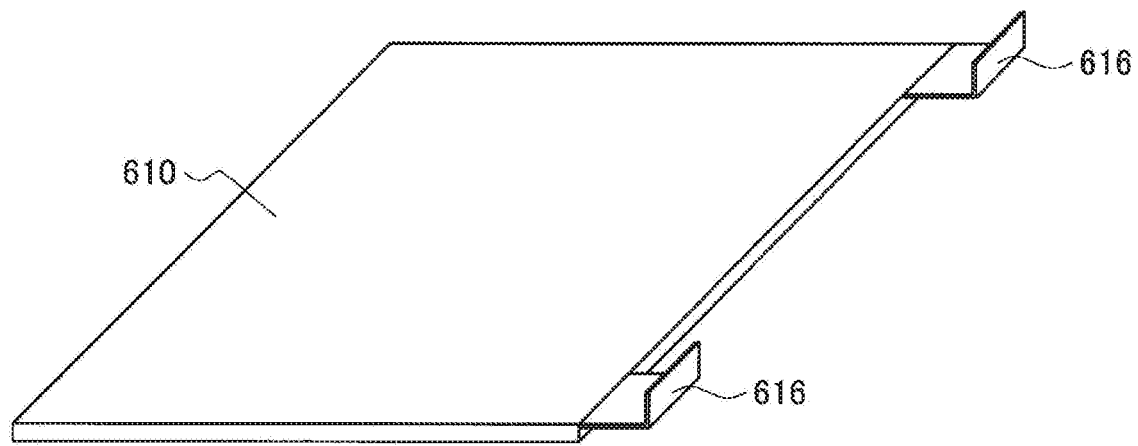
FIG. 21 is a diagram illustrating an example of a holder provided on the screen of the embodiment of the present disclosure.
Figure 22:
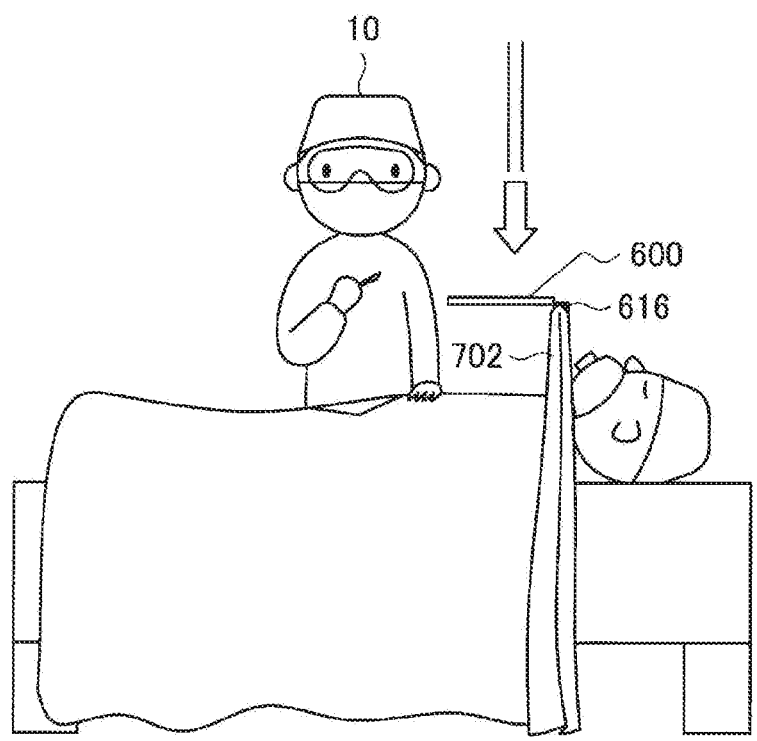
FIG. 22 is a diagram illustrating an installation example of the screen of the embodiment of the present disclosure.

In addition, the holder 616 may be provided on the side surface of the screen 600 as illustrated in FIG. 21. At this time, the screen 600 may be fixed to the frame as illustrated in FIG. 22.

<2-3. Other Configuration Examples of Screen>

Heretofore, the installation method of the screen 600 used in the present embodiment has been described. Hereinafter, another configuration example of the screen 600 will be described. Since the screen 600 of the present embodiment is used for medical practice, the screen is required to be clean. Therefore, it is preferable that the screen 600 is disposable. At this time, since the screen 600 includes a plastic resin, the holder 616 can be molded integrally with the screen 600, and thus, the screen 600 can be manufactured at a very low cost. The screen 600 is manufactured at a low cost, so that the screen 600 can be configured so as to be disposable, and the reliability of cleanliness can be improved. In addition, the configuration as the optical characteristics of the screen 600 may be configured by using a coating method or the like.

In addition, it is preferable that sterilization treatment can be applied to the screen 600. Thus, the material of the screen 600 is preferably a material that can withstand sterilization, can be made inexpensively, and can form a membrane. In addition, since it is preferable that the flatness of the screen 600 be maintained when the screen 600 is fixed, the material of the screen 600 is required to have a certain degree of hardness. Therefore, the screen 600 preferably includes a material such as polystyrene, polycarbonate, polymethyl methacrylate resin, acrylic resin, or polysulfone. In addition, the material of the screen 600 may be high-density polyethylene or fluorocarbon resin, and at this time, the surface modification or the like is performed to facilitate formation of the selective reflection layer 610 and the like.

In addition, it is assumed that the screen 600 of the present embodiment is used in the environment where liquid such as blood is adhered to the surface of the screen 600 in surgery or the like. Therefore, it is preferable that water repellent treatment is applied to the surface of the screen 600. In this manner, the water repellent treatment is applied to the surface of the screen 600, so that the assistant can easily remove the liquid with the gauze. As an example of the water repellent treatment, there may be exemplified a method in which the screen is applied with a fluorine resin having a thickness of several nm where optical influence does not appear, a method in which the surface of the screen 600 is coated with a water repellent material by film formation, and the like.

3. Hardware Configuration

Figure 23:
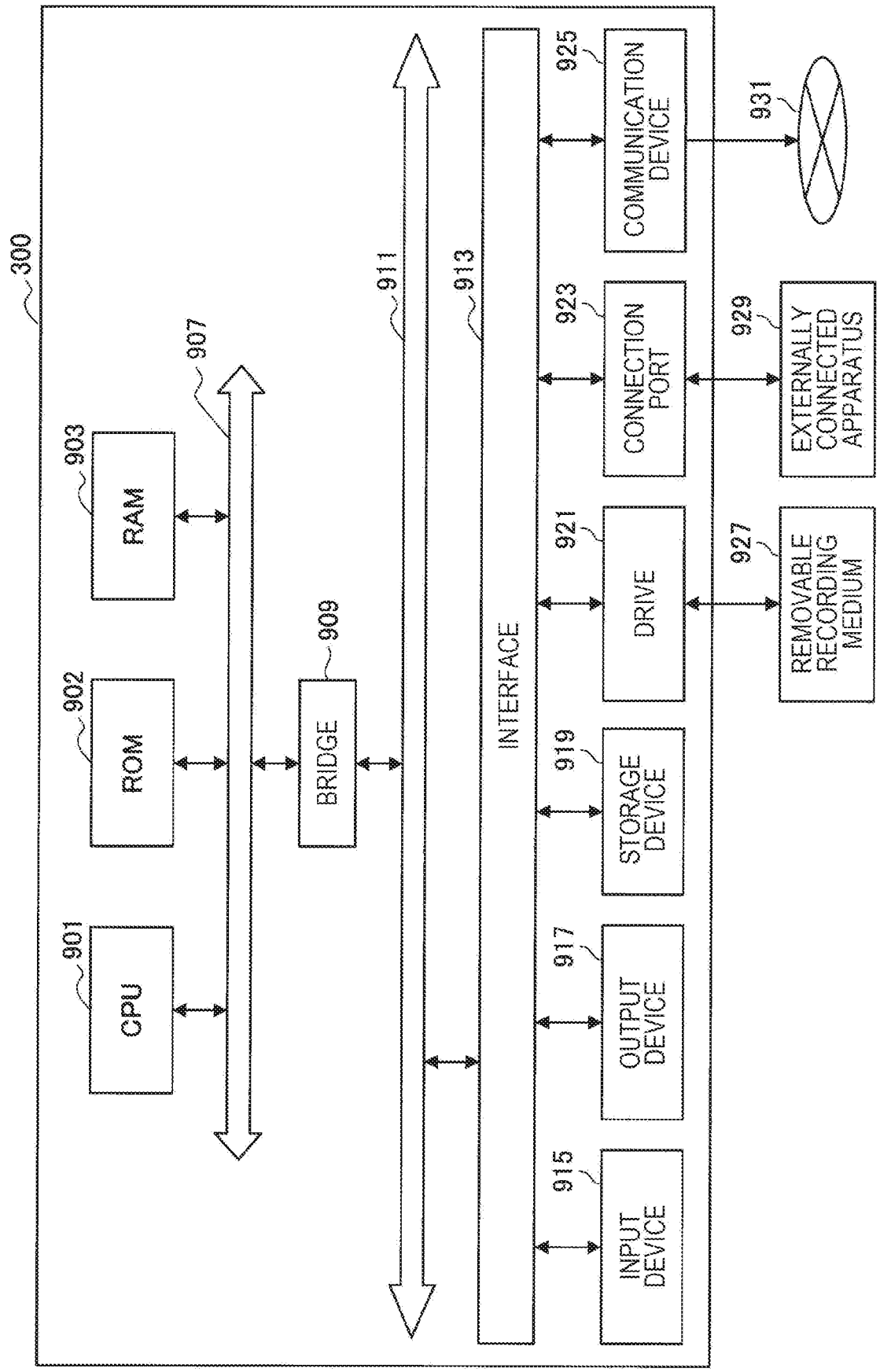
FIG. 23 is a block diagram schematically illustrating an example of a hardware configuration of a controller on the embodiment of the present disclosure.

Hereinafter, the hardware configuration of the controller 300 of the embodiment of the present disclosure will be described in detail with reference to FIG. 23. FIG. 23 is a block diagram illustrating the hardware configuration of the controller 300 according to an embodiment of the present disclosure.

The controller 300 mainly includes a CPU 901, a ROM 903, and a RAM 905. In addition, the controller 300 further includes a host bus 907, abridge 909, an external bus 911, an interface 913, an input device 915, an output device 917, a storage device 919, a drive 921, a connection port 923, and a communication device 925.

The CPU 901 functions as a central processing unit and a control unit and controls the overall operations or a part of the operations in the controller 300 in accordance with various programs recorded in the ROM 903, the RAM 905, the storage device 919, or a removable recording medium 927. The ROM 903 stores programs, calculation parameters, and the like used by the CPU 901. The RAM 905 primarily stores programs used by the CPU 901, parameters that appropriately change in the execution of the programs, and the like. The ROM and the RAM are connected to each other via the host bus 907 configured with an internal bus such as a CPU bus.

The host bus 907 is connected to an external bus 911 such as a peripheral component interconnect/interface (PCI) bus via the bridge 909.

The input device 915 is a manipulation unit manipulated by the user, such as a mouse, a keyboard, a touch panel, a button, a switch, and a lever, for example. In addition, the input device 915 may be a remote control unit (so-called remote controller) using, for example, infrared rays or other radio waves or may be an externally connected apparatus 929 such as a mobile phone or PDA corresponding to the manipulation of the controller 300. Furthermore, the input device 915 may be configured with an input control circuit or the like that generates an input signal on the basis of the information input by the user by using, for example, the above-described manipulation units and outputs the generated input signal to the CPU 901. By manipulating the input device 915, the user can input various data to the controller 300 and instruct processing operations.

The output device 917 is configured with a device capable of visually or aurally notifying the user of the acquired information. As such a device, there may be exemplified a display device such as a CRT display device, a liquid crystal display device, a plasma display device, an EL display device, and a lamp, an audio output device such as a speaker and a headphone, a printer device, a mobile phone, a facsimile, and the like. The output device 917 outputs results obtained by various processes performed by, for example, the controller 300. Specifically, the display device displays the result obtained by the various processes performed by the controller 300 as a text or an image. On the other hand, the audio output device converts an audio signal including reproduced audio data, acoustic data, and the like into an analog signal and outputs the analog signal.

The storage device 919 is a device for data storage configured as an example of a storage unit of the controller 300. The storage device 919 is configured with, for example, a magnetic storage device such as a hard disk drive (HDD), a semiconductor storage device, an optical storage device, a magneto-optical storage device, or the like. The storage device 919 stores programs or various data executed by the CPU 901 and various data acquired from the outside, and the like.

The drive 921 is a reader/writer for a recording medium and is built in or externally attached to the controller 300. The drive 921 reads out information recorded in the mounted removable recording medium. 927 such as a magnetic disk, an optical disk, a magneto-optical disk, or a semiconductor memory and outputs the information to the RAM 905. In addition, the drive 921 can also write a record on the mounted removable recording medium 927 such as a magnetic disk, an optical disk, a magneto-optical disk, or a semiconductor memory. The removable recording medium 927 is, for example, a DVD medium, an HD-DVD medium, a Blu-ray (registered trademark) medium, or the like. In addition, the removable recording medium 927 may be compact flash (CF (registered trademark)), a flash memory, a secure digital (SD) memory card, or the like. In addition, the removable recording medium 927 may be, for example, an integrated circuit card (IC card) equipped with a non-contact IC chip, an electronic device, or the like.

The connection port 923 is a port for directly connecting the device to the controller 300. As an example of the connection port 923, there may be exemplified a universal serial bus (USB) port, an IEEE 1394 port, a small computer system interface (SCSI) port, and the like. As another example of the connection port 923, there may be exemplified an RS-232C port, an optical audio terminal, a high-definition multimedia interface (HDMI (registered trademark)) port, and the like. The externally connected apparatus 929 is connected to the connection port 923, so that the controller 300 acquires various data directly from the externally connected apparatus 929 and provides various data to the externally connected apparatus 929.

The communication device 925 is a communication interface configured with a communication device or the like for connecting to, for example, a communication network 931. The communication device 925 is a communication card for, for example, wired or wireless local area network (LAN), Bluetooth (registered trademark), wireless USB (WUSB), or the like. In addition, the communication device 925 may be a router for optical communication, a router for asymmetric digital subscriber line (ADSL), a modem for various types of communication, or the like. The communication device 925 can transmit and receive signals and the like in accordance with a predetermined protocol such as TCP/IP or the like from and to, for example, the Internet or another communication device. In addition, the communication network 931 connected to the communication device 925 is configured with a network or the like connected in a wired or wireless manner and may be, for example, the Internet, home LAN, infrared communication, radio wave communication, satellite communication, or the like.

4. Supplement

Heretofore, the preferred embodiments of the present disclosure have been described in detail with reference to the accompanying drawings, but the technical scope of the present disclosure is not limited to such embodiments. It will be apparent to those skilled in the art of the present disclosure that various modifications and alterations can be conceived within the scope of the technical idea described in the claims and belong to the technical scope of the present disclosure.

For example, instead of the information selection unit 306 determining in S210 of FIG. 9 that the numerical information from the information providing device 100 has reached the predetermined threshold, the information selection unit 306 may detect that the numerical information from the information providing device 100 has been changed to be the predetermined threshold or more for a predetermined period and may select the changed information as the information to be drawn. The information drawing device 200 according to the present embodiment is configured in this manner, so that for example, the medical practitioner can recognize that there is a large amount of bleeding.

In addition, the information selected by the information selection unit 306 in S204, S208, S212, and S216 of FIG. 9 maybe displayed only for a predetermined time. For example, in a case where the information selection unit 306 detects that the power of the information providing device 100 is turned on in S202 and selects the information related to the information providing device 100 where the power is turned on in S204 as the information to be drawn, the selected information may be displayed only for a predetermined time (for example, several seconds). The information drawing device 200 according to the present embodiment is configured in this manner, so that it is possible to prevent the information that needs not to be always displayed from being continuously displayed on the screen 600.

In addition, when it is detected in S202 or S214 of FIG. 9 that there has been a change in the operation state of the information providing device 100 or that the setting value of the information providing device 100 has been changed, an indication denoting that the operation state or the setting value has been changed may be displayed on screen 600 together with the numerical information and the header information. For example, a message indicating "changed" together with the numerical information and the header information may be displayed on the screen 600.

In addition, a plurality of the screens 600 described above may be arranged, and an irradiation unit that irradiates each of the plurality of arranged screens 600 with the drawing light may be provided. The plurality of screens 600 are arranged in this manner, so that more information is presented to the medical practitioner.

In addition, the controller 300 described above may be realized by using a general purpose processor. In addition, a computer program may be provided to operate the processor as described in FIGS. 7 and 9. In addition, a storage medium in which such a program is stored may be provided.

5. Conclusion

As described above, in the information drawing system according to the present disclosure, the drawing light having illuminance visually recognizable under the light of the shadowless lamp 800 causes quantitative numerical values such as the setting value of the device, the blood pressure value, and the amount of bleeding to be drawn on the screen 600. With this configuration, the medical practitioner can visually check the quantitative numerical values, so that an accident due to mishearing can be prevented. In addition, unnecessary conversation between the operator 10 and the assistant is reduced, and the burden on the operator 10 is reduced. In addition, the reduction of unnecessary conversation between the operator 10 and the assistant leads to shortening of a time of the surgical operation.

In addition, in the information drawing system according to the present disclosure, the screen 600 which selectively reflects the wavelength of the drawing light is used. Thus, the medical practitioner can easily view the information drawn by the drawing light under the light of the shadowless lamp 800.

In addition, the following configurations are also within the technical scope of the present disclosure.

(1)

An information processing device including:

an information acquisition unit that acquires information from an information providing device that provides the information related to quantitative numerical values to be grasped by a medical practitioner involved with a medical practice;

an image data generation unit that generates image data related to the acquired information; and a control unit that controls an installation position of a light source irradiating drawing light having illuminance visually recognizable under a shadowless lamp or an operation state of an optical system that scans an irradiation position of the drawing light so as to draw the image data.

(2)

The information processing device according to (1), in which the light source is a laser source.

(3)

The information processing device according to (1) or (2), in which the information acquisition unit acquires header information indicating a type of the information together with the information related to the quantitative numerical value.

(4)

The information processing device according to any one of (1) to 3, further including: an information selection unit that selects the information to be drawn from the information acquired by the information acquisition unit from the information providing device.

(5)

The information processing device according to (4), in which the information selection unit selects the information to be drawn on the basis of an output from a manipulation unit manipulated by a medical practitioner.

(6)

The information processing device according to (4), further including a storage unit that stores a database in which a medical practice and the information to be drawn are associated with each other, in which the information selection unit selects the information to be drawn according to the medical practice with reference to the database.

(7)

The information processing device according to (4), in which the information selection unit selects the information to be displayed according to a change of a setting value of the information providing device.

(8)

The information processing device according to (4), in which the information selection unit selects the information to be displayed according to an operation state of the information providing device.

(9)

The information processing device according to (4), in which the information selection unit selects the information to be displayed on the basis of a change in a numerical value measured by the information providing device.

(10)

The information processing device according to (9), in which the information selection unit selects the information to be displayed on the basis of a fact that the numerical value measured by the information providing device has reached a predetermined threshold.

(11)

The information processing device according to any one of (1) to 10, in which the information acquisition unit processes a captured image from an imaging device that images information displayed on the information providing device, and acquires the information related to the information providing device.

(12)

An information processing method including:

acquiring information from an information providing device that provides the information related to a medical practice or a condition of a patient;

generating image data related to the acquired information; and controlling an installation position of a light source irradiating drawing light having illuminance visually recognizable under a shadowless lamp or an operation state of an optical system that scans an irradiation position of the drawing light so as to draw the image data.

(13)

A program causing a processor to execute:

acquiring information from an information providing device that provides the information related to a medical practice or a condition of a patient;

generating image data related to the acquired information; and controlling an operation state of an optical system that scans an installation position of a light source irradiating drawing light having illuminance visually recognizable under a shadowless lamp or an irradiation position of the drawing light so as to draw the image data.

(14)

A screen including;

a substrate including a predetermined material; and a selective reflection layer having a reflectance for a wavelength of drawing light from an information drawing device that draws an image by using the drawing light having illuminance visually recognizable under a shadowless lamp, the reflectance being higher than a reflectance for wavelengths of other light, on the substrate.

(15)

The screen according to (14), in which the selective reflection layer is configured with a multilayer film in which materials having different refractive indexes are alternately stacked.

(16)

The screen according to (14) or (15), further including a holder for placing the screen within a field of view of a medical practitioner on a side opposite to a surface on which the selective reflection layer is formed or on a side surface of the screen.

(17)

The screen according to (16), in which the holder is bendable.

(18)

The screen according to any one of (14) to 17, further including a water repellent layer on the selective reflection layer.

(19)

An information drawing system including:

an information drawing device including:

a light source that irradiates drawing light having illuminance visually recognizable under a shadowless lamp;

an optical system that scans an irradiation position of the drawing light;

an information acquisition unit that acquires information from an information providing device that provides the information related to quantitative numerical values to be grasped by a medical practitioner involved with a medical practice;
an image data generation unit that generates image data related to the acquired information; and
a control unit that controls an installation position of the light source or an operation state of the optical system so as to draw the image data; and
a screen including:
a substrate including a predetermined material; and
a selective reflection layer having a reflectance for a wavelength of the drawing light from the information drawing device, the reflectance being higher than a reflectance for a wavelength of other light, on the substrate.

REFERENCE SIGNS LIST

10 Operator
12 Instrument transfer assistant
14 Outer circumference assistant
16 Anesthesiologist
18 Patient
100 Information providing device
120 Imaging device
200 Information drawing device
300 Controller
302 Manipulation unit
304 Information acquisition unit
306 Information selection unit
308 Image data generation unit
310 Control unit
312 Storage unit
400 Light source
402 Light irradiation unit
500 Optical system
502 Scan mirror
504 Scan lens
506 Imaging lens
600 Screen
602 Header information display area
604 Numerical information display area
606 Substrate
608 Light absorption layer
610 Selective reflection layer
612 High refractive index film
614 Low refractive index film
616 Holder
700 Drape
800 Shadowless lamp

The invention claimed is:

1. An information processing device comprising:
a processor configured to:
store a database in which a plurality of medical practices and a plurality of quantitative numerical values are associated with each other;
acquire information from an information providing device, wherein the information includes the plurality of quantitative numerical values to be grasped by a medical practitioner involved with a medical practice of the plurality of medical practices;
estimate a type of the medical practice the medical practitioner is involved with based on a time elapsed from a start of a surgical operation;
select a quantitative numerical value to be drawn from the plurality of quantitative numerical values based on an association of the medical practice and the quantitative numerical value in the stored database, a change in the quantitative numerical value, and the estimated type of the medical practice;
generate image data related to the selected quantitative numerical value; and
control an installation position of a light source irradiating drawing light having illuminance visually recognizable under a shadowless lamp or an operation state of an optical system that scans an irradiation position of the drawing light so as to draw the image data.

2. The information processing device according to claim 1, wherein the light source is a laser source.

3. The information processing device according to claim 1, wherein the processor is further configured to acquire header information indicating a type of the information related to the quantitative numerical value.

4. The information processing device according to claim 1, wherein the selection of the quantitative numerical value to be drawn is further based on an output from a manipulation device manipulated by the medical practitioner.

5. The information processing device according to claim 1, wherein the selection of the quantitative numerical value to be drawn is further based on a change of a setting value of the information providing device.

6. The information processing device according to claim 1, wherein the selection of the quantitative numerical value to be drawn is further based on an operation state of the information providing device.

7. The information processing device according to claim 1, wherein the selection of the quantitative numerical value to be drawn is further based on a fact that the quantitative numerical value measured by the information providing device has reached a predetermined threshold.

8. The information processing device according to claim 1, wherein the processor is further configured to process a captured image from an imaging device that images information displayed on the information providing device to acquire the information from the information providing device.

9. An information processing method comprising:
storing, by a processor, a database in which a plurality of medical practices and a plurality of quantitative numerical values are associated with each other;
acquiring, by the processor, information from an information providing device that provides the information related to a medical practice of the plurality of medical practices or a condition of a patient, wherein the information includes the plurality of quantitative numerical values to be grasped by a medical practitioner involved with the medical practice;
estimating, by the processor, a type of the medical practice the medical practitioner is involved with based on a time elapsed from a start of a surgical operation;
selecting, by the processor, a quantitative numerical value to be drawn from the plurality of quantitative numerical values based on an association of the medical practice and the quantitative numerical value in the stored database, a change in the quantitative numerical value, and the estimated type of the medical practice;
generating, by the processor, image data based on the selected quantitative numerical value; and
controlling, by the processor, an installation position of a light source irradiating drawing light having illuminance visually recognizable under a shadowless lamp or an operation state of an optical system that scans an irradiation position of the drawing light so as to draw the image data.

10. A non-transitory computer-readable medium, having stored thereon, computer-executable instructions that, when executed by a computer, cause the computer to execute operations, the operations comprising:
storing a database in which a plurality of medical practices and a plurality of quantitative numerical values are associated with each other;
acquiring information from an information providing device that provides the information related to a medical practice of the plurality of medical practices or a condition of a patient, wherein the information includes the plurality of quantitative numerical values to be grasped by a medical practitioner involved with the medical practice;
estimating a type of the medical practice the medical practitioner is involved with based on a time elapsed from a start of a surgical operation;
selecting a quantitative numerical value to be drawn from the plurality of quantitative numerical values based on an association of the medical practice and the quantitative numerical value in the stored database, a change in the quantitative numerical value, and the estimated type of the medical practice;
generating image data based on the selected quantitative numerical value; and
controlling an operation state of an optical system that scans an installation position of a light source irradiating drawing light having illuminance visually recognizable under a shadowless lamp or an irradiation position of the drawing light so as to draw the image data.

11. An information drawing system comprising:
an information drawing device including:
a light source configured to irradiate drawing light having illuminance visually recognizable under a shadowless lamp;
an optical system configured to scan an irradiation position of the drawing light;
a processor configured to:
store a database in which a plurality of medical practices and a plurality of quantitative numerical values are associated with each other;
acquire information from an information providing device, wherein the information includes the plurality of quantitative numerical values to be grasped by a medical practitioner involved with a medical practice of the plurality of medical practices;
estimate a type of the medical practice the medical practitioner is involved with based on a time elapsed from a start of a surgical operation;
select a quantitative numerical value to be drawn from the plurality of quantitative numerical values based on an association of the medical practice and the quantitative numerical value in the stored database, a change in the quantitative numerical value, and the estimated type of the medical practice;
generate image data related to the selected quantitative numerical value; and
control an installation position of the light source or an operation state of the optical system so as to draw the image data; and
a screen including:
a substrate including a predetermined material; and
a selective reflection layer having a reflectance for a wavelength of the drawing light from the information drawing device, the reflectance being higher than a reflectance for a wavelength of other light, on the substrate.

12. The information drawing system according to claim 11, wherein the selective reflection layer is configured with a multilayer film in which materials that have different refractive indexes are alternately stacked.

13. The information drawing system according to claim 11, wherein the screen further comprises a holder to place the screen within a field of view of the medical practitioner on a side opposite to a surface on which the selective reflection layer is formed or on a side surface of the screen.

14. The information drawing system according to claim 13, wherein the holder is bendable.

15. The information drawing system according to claim 11, wherein the screen further comprises a water repellent layer on the selective reflection layer.

16. The information processing device according to claim 1, wherein the processor is further configured to:
detect whether a frequency of a word related to the medical practice and spoken by the medical practitioner is greater than a predetermined frequency; and
estimate the type of the medical practice that the medical practitioner is involved with further based on a detection that the frequency of the word is greater than the predetermined frequency.

* * * * *